US007183388B2

(12) United States Patent
Denardo et al.

(10) Patent No.: US 7,183,388 B2
(45) Date of Patent: Feb. 27, 2007

(54) ANTI-MUC-1 SINGLE CHAIN ANTIBODIES FOR TUMOR TARGETING

(75) Inventors: Sally Joan Denardo, El Macero, CA (US); Michelle Denise Winthrop, Woodland, CA (US); Gerald Louis Denardo, El Macero, CA (US); Cheng-Yi Xiong, Elk Grove, CA (US)

(73) Assignee: The Regents of the University of California, Oakland, CA (US)

( * ) Notice: Subject to any disclaimer, the term of this patent is extended or adjusted under 35 U.S.C. 154(b) by 186 days.

(21) Appl. No.: 10/435,614

(22) Filed: May 9, 2003

(65) Prior Publication Data

US 2004/0005647 A1    Jan. 8, 2004

Related U.S. Application Data

(63) Continuation-in-part of application No. 10/122,788, filed on Mar. 28, 2002.

(60) Provisional application No. 60/280,721, filed on Mar. 30, 2001.

(51) Int. Cl.
*C07K 16/00* (2006.01)
*C12P 21/08* (2006.01)
*A61K 39/395* (2006.01)
*C12P 21/04* (2006.01)

(52) U.S. Cl. .............. 530/387.3; 530/388.1; 530/388.22; 530/388.85; 530/391.3; 530/391.7; 424/133.1; 424/135.1; 424/141.1; 424/143.1; 424/156.1; 424/181.1; 424/183.1; 435/69.6

(58) Field of Classification Search ............ 530/387.1, 530/387.3, 388.1, 388.8, 391.3, 391.7, 388.22, 530/388.85; 424/130.1, 133.1, 135.1, 141.1, 424/155.1, 181.1, 183.1, 143.1, 156.1; 435/69.6
See application file for complete search history.

(56) References Cited

U.S. PATENT DOCUMENTS

| 5,506,343 | A | | 4/1996 | Kufe |
|---|---|---|---|---|
| 5,744,144 | A | | 4/1998 | Finn et al. |
| 5,827,666 | A | | 10/1998 | Finn et al. |
| 5,846,746 | A | | 12/1998 | Gipson |
| 5,851,829 | A | * | 12/1998 | Marasco et al. |
| 6,114,129 | A | | 9/2000 | Agrawal et al. |
| 6,224,866 | B1 | | 5/2001 | Barbera-Guillem |
| 6,245,752 | B1 | | 6/2001 | Barbera-Guillem et al. |
| 6,251,616 | B1 | | 6/2001 | Barbera-Guillem et al. |
| 6,365,124 | B1 | | 4/2002 | Babino et al. |
| 6,387,888 | B1 | | 5/2002 | Mincheff et al. |
| 6,418,338 | B1 | | 7/2002 | Barbera-Guillem et al. |
| 6,514,942 | B1 | | 2/2003 | Ioannides et al. |
| 6,521,404 | B1 | | 2/2003 | Griffiths et al. |
| 6,544,731 | B1 | | 4/2003 | Griffiths et al. |
| 6,548,643 | B1 | | 4/2003 | McKenzie et al. |
| 6,555,313 | B1 | | 4/2003 | Griffiths et al. |

FOREIGN PATENT DOCUMENTS

| WO | WO 96/03502 | 2/1996 |
|---|---|---|
| WO | WO 99/40881 | 8/1999 |

OTHER PUBLICATIONS

Alberts et al. Molecular Biology of the Cell, 3rd ed, pp. 1216-1218, 1994.*
Coleman P. M. Research in Immunology, 145:33-36, 1994.*
Barratt-Boys (1996) "Making the most of mucin: a novel target for tumor immunotherapy." *Cancer Immunol Immunother* 43:142-151.
Bieche and Lidereau (1997) "A Gene Dosage Effect Is Responsible for High Overexpression of the MUC1 Gene Observed in Human Breast Tumors." *Cancer Genet Cyogenet* 98:75-80.
Clackson et al. (1991) "Making antibody fragements using phage display libraries." *Nature* 352:624-628.
Denardo et al. (1991) "Quantitive Imaging of Mouse L-6 Monoclonal Antibody in Breast Cancer Patients to Develop a Therapeutic Strategy." *Nucl. Med. Biol.* 18(6):621-631.
Denardo et al. (1997) "Radioimmunotherapy for Breast Cancer Using Indium-111/Yttrium-90 BrE-3: Results of a Phase I Clinical Trial" *The Journal of Nuclear Medicine* 38(8) 1180-1185.
Dong et al. (1997) "Expression of MUC1 and MUC2 Mucins in Epithelial Ovarian Tumors." *Journal of Pathology* 183:311-317.
Fontenot et al. (1993) "Biophysical Characterization of One-, Two-, and Three-Tandem Repeats of Human Mucin (muc-1) Protein Core." *Cancer Research* 53:5386-5394.
Henderson et al. (1998) "Retroviral Expression of MUC-1 Human Tumor Antigen with Intact Repeat Structure and Capacity to Elicit Immunity In Vivo." *Journal of Immunotherapy*. 21 (4): 247-256.
Hoogenboom et al. (1998) "Antibody phage display technology and its applications."0 *Immunothechnology* 4:1-20.
Kotera et al. (1994) "Munoral Immunity against a Tandem Repeat Epitope of Human Mucin MUC-1 in Sera from Breast, Pancreatic, and Colon Cancer Patients." *Cancer Research* 54:2856-2860.
Lipcon et al. (1998) "Initial Clinical Evaluation of Radiolabeled MX-DTPA Humanized BrE-3 Antibody in Patients with Advanced Breast Cancer." *Clinical Cancer Research* 4:1679-1688.
Maraveyas et al. (1994) "Pharmacokinetics and Toxicity of an Yttrium -90-CITC-DTPA-HMFG1 Radioimmunoconjugate for Intraperitoneal Radioimmunotherapy of Ovarian Cancer." *Cancer* 73:1067-1075.
Maziere et al. (1986) "Early Increase in Phosphatidyl Choline Synthesis by Choline and Transmethylation Pathways in Spreading Fibroblasts." *Ex. Cell Res.* 167:257-261.

(Continued)

*Primary Examiner*—Sheela J. Huff
*Assistant Examiner*—David J. Blanchard
(74) *Attorney, Agent, or Firm*—Beyer Weaver LLP; Tom Hunter

(57) ABSTRACT

This invention provides novel antibodies that specifically bind to the cancer antigen MUC-1. The antibodies are useful targeting moieties for specifically directing imaging agents and various therapeutic moieties to a cancer.

28 Claims, 5 Drawing Sheets

OTHER PUBLICATIONS

McGuckin et al. (1995) "Prognostic Significance of MUC1 Epithelial Mucin Expreaaion in Breast Cancer." *Human Pathology* 26:432-439.

Taylor-Papadimitriou et al. (1999) "MUC1 and Cancer." *Biochimica et Biophysical Acta* 1455:301-313.

Pavlinkova et al. (1999) "Pharmacokinetics and Biodistribution of Engineered Single-Chain Antibody Constructs of Mab CC49 in Colon Carcinoma Xenografts." *The Journal of Nuclear Medicine* 40(9):1536-1546.

Pemberton et al. (1996) "The Epithelial Mucin MUC1 Contains at Least Two Discrete Signals Specifying Membrane Localization of Cells." *The Journal of Biological Chemistry* 271(4): 2332-2340.

Peterson et al. (1991) "Molecular Analysis of Epitopic Heterogeneity of the Breast Mucin." *Breast Epithelial Antigens* pp. 55-68.

Press et al. (1993) "Radiolameled-antibody Therapy of B-Cell Lymphoma with Autologous Bone Marrow Support." *The New Endland Journal of Medicine* 329(17): 1219-1224.

Price et al. (1998) "Summary Report on the ISOBM TD-4 Workshop: Analysis of 56 Monoclonal Antibodies against the MUC1 Mucin." *Tumor Biology* 16:1-20.

Quin and McGuckin (2000) "Phosphorylation of the Cytoplasmic Domain of the MUC1 Mucin Correlates with Changes in Cell—Cell Adhesion." *Int. J. Cancer* 87:499-506.

Regimbald et al. (1996) "The Breast Mucin MUC1 as a Novel Adhesion Ligand for Endothelial Intracellular Adhesion Molecule 1 in Breast Cancer." *Cancer Research* 56:4244-4249.

Stewart and Brunjes (1993) "Spatial organization and plasticity of the primary and secondary olfactory projections in goldfish." *Brain Research* 628:243-253.

Viti et al. (1999) "Increased Binding Affinity and Valence of Recombinant Antibody Fragments Lead to Improved Targeting of Tumoral Angiogenesis." *Cancer Research* 59:347-352.

Winter et al. (1994) Making Antibodies by Phage Display Technology. *Annu. Rev. Immunology* 12:433-455.

Asano et al. (2000) J. Biochem. vol. 127 pp. 673-679.

Apostolopoulos et al. (1994) Critical Reviews in Immunology vol. 14, No. 3&4, pp. 293-309.

Bandyopadhyay et al. (2002) Intl. Journal of Cancer Supplement No. 13, p. 88.

Denton (1999) Cancer Immunol Immunother. 48: pp. 29-38.

Fiorentini et al. (1997) Immunotechnology vol. 3, pp. 45-49.

Hartman et al. (1999) Intl. Journal of Cancer (82) pp. 256-267.

Hoogenboom et al. (2000) Immunology Today vol. 21, No. 8, pp. 371-378.

Hudson (1999) Current Biology Ltd. vol. 11, No. 5, pp. 548-557.

Paul (1993) Fundamental Immunology, $3^{rd}$ Ed. pp. 292-295.

Price et al. (1998) Tumor Biol. 19: pp. 1-20.

Rudikoff et al. (1982) Proc. Natl. Acad. Sci. USA (79) pp. 1979-1983.

* cited by examiner

ANTI-MUC-1 SINGLE CHAIN ANTIBODIES FOR TUMOR TARGETING

CROSS-REFERENCE TO RELATED APPLICATIONS

This application is a continuation-in-part of U.S. Ser. No. 10/112,788, filed on Mar. 28, 2002, which claims priority to U.S. Ser. No. 60/280,721, filed on Mar. 30, 2001, both of which are incorporated herein by reference in their entirety for all purposes.

STATEMENT AS TO RIGHTS TO INVENTIONS MADE UNDER FEDERALLY SPONSORED RESEARCH AND DEVELOPMENT

This work was supported by National Cancer Institute Grant CA-47829, California Breast Cancer Research Program Postdoctoral Fellowship Grant 5FB-0023, and Society of Nuclear Medicine Education and Research Fellowship. The Government of the United States of America may have certain rights in this invention.

FIELD OF THE INVENTION

This application pertains to the field of antibody engineering. In particular, antibodies are provided that specifically bind to the MUC-1 cancer antigen.

BACKGROUND OF THE INVENTION

Recombinant antibodies and their fragments have become key to the design of high affinity specific targeting drugs. Recent construction of engineered targeting molecules has demonstrated the need for use of minimal binding fragments that are rebuilt into multivalent high affinity reagents. Antibody fragment units have also been found with a range of molecules for gene therapy, imaging, immunotherapy, radiotherapy, chemotherapy and pro-drug therapy. ScFv (30 kD) are usually the smallest antibody fragment that retains specific binding characteristics. ScFv are produced by randomly connecting the variable heavy ($V_H$) and variable light ($V_L$) chain immunoglobulin genes together using a biologically inert flexible linker. While scFv molecules have been produced from existing monoclonal antibodies, phage display libraries now provide a multitude of scFv from a single source, allowing those with optimal binding characteristics to be simultaneously selected along with the genes encoding the displayed scFv (1. Pavlinkova et al. (1999) *J Nucl Med*, 40:1536–1546; Viti et al. (1999) *Cancer Res*, 59: 347–352; Winter et al. (1994)*Annu. Rev. Immunol*, 12: 433–455; Clackson et al. (1991) *Nature*, 352: 624–628; Hoogenboom et al. (1998) *Immunotechnology*, 4: 1–20; *Phage display of peptides and proteins: a laboratory manual*. San Diego: Academic Press, 1996).

One of the epithelial mucin family of molecules, MUC-1 has received considerable interest as an antigen target because it is widely expressed on a large number of epithelial cancers and is aberrantly glycosylated making it structurally and antigenically distinct from that expressed by non-malignant cells (Barratt-Boyes (1996) *Cancer Immunol Immunother*, 43: 142–151; Price et al. (1998) *Tumor Biology*, 19: 1–20; Peterson et al. (1991), Pages 55–68 In: *Breast Epithelial Antigens*, R. L. Ceriani. (ed.), New York: Plenum Press). The dominant form of MUC-1 is a high molecular weight molecule comprised of a large highly immunogenic extracellular mucin-like domain with a large number of 20 amino acid tandem repeats, a transmembrane region, and a cytoplasmic tail (Quin et al. (2000) *Int J Cancer*, 87:499–506; McGucken et al. (1995) *Human Pathology*, 26: 432–439; Dong et al. (1997) *J. Pathology*, 183: 311–317). In normal epithelial tissue, MUC-1 is localized to the apical region of the cells; malignant transformation results in upregulation of MUC-1 by gene amplification and/or increased transcriptional activation and the distribution of MUC-1 on the cell surface is no longer confined to the apical region (Bieche and Lidereau (1997) *Cancer Genetics and Cytogenetics*, 98: 75–80). While the function of MUC-1 still awaits clarification, high cytoplasmic expression of MUC-1 expression have been associated with poor prognosis in patients with breast and/or ovarian cancers. MUC-1 has also been demonstrated to play a role in cell adhesion, cell signaling and immune responses (Quin et al. (2000) *Int J Cancer*, 87:499–506; McGucken et al. (1995) *Human Pathology*, 26: 432–439; Dong et al. (1997) *J. Pathology*, 183: 311–317; Henderson et al. (1998) *J Immunother*, 21: 247–256).

A substantial number of anti-MUC-1 monoclonal antibodies (MoAb) have been produced with the majority of these MoAb recognizing epitopes contained within the twenty amino acid tandem repeat that are bordered on each side by a serine and a threonine (Barratt-Boyes (1996) *Cancer Immunol Immunother*, 43: 142–151.; Price et al. (1998) *Tumor Biology*, 19: 1–20; Peterson et al. (1991), Pages 55–68 In: *Breast Epithelial Antigens*, R. L. Ceriani. (ed.), New York: Plenum Press; Fontenot et al. (1993) *Cancer Res*, 53: 5386–5394 Pemberton et al. (1996) *J Biol. Chem.*, 271: 2332–2340; Regimbald et al. (1996) *Cancer Res*, 56: 4244–4249; Kotera et al. (1994) *Cancer Res*, 54: 2856–2860). These anti-MUC-1 MoAbs have been used primarily as diagnostic agents to identify tumors and monitor levels of circulating antigen. A few MUC-1 MoAbs have been used to deliver targeted radiation to tumors as radioimmunotherapy. In ovarian cancer, the HMFG1 antibody was used to deliver high dose yttrium to the peritoneum in patients with minimal residual disease after receiving chemotherapy (Papadimitriou et al. (1999) *Biochimica et. Biophysica Acta*, 1455: 301–313; Maraveyas et al. (1994) *Cancer*, 73: 1067–1075). A clear survival benefit was demonstrated when compared to historical controls (Id.). The results were significant enough to prompt a phase III multicenter trial for treatment of ovarian cancer. Another anti-MUC-1 MoAb (BrE-3) labeled with $^{90}Y$ has also been used in the treatment of breast cancer (Papadimitriou et al. (1999) *Biochimica et. Biophysica Acta*, 1455: 301–313; DeNardo et al. (1997) *J Nucl Med*, 38: 1180–1185; Kramer et al. (1998) *Clin Cancer Res*, 4: 1679–1688; Press et al. (1993) *N Engl J Med*, 329: 1219–1224). Transient clinical response warrants further studies (Papadimitriou et al. (1999) *Biochimica et. Biophysica Acta*, 1455: 301–313; DeNardo et al. (1997) *J Nucl Med*, 38: 1180–1185; Kramer et al. (1998) *Clin Cancer Res*, 4: 1679–1688; Press et al. (1993) *N Engl J Med*, 329: 1219–1224; DeNardo et al. (1991) *Int J Rad Appl Instrum [B]*. 18: 621–631; Stewart and Brunjes (1993) *Brain Res*. 628: 243–253).

While radioimmunotherapy using intact MoAbs has been utilized in the treatment of breast cancer and other solid tumors, therapeutic success has been limited by the large size of the MoAb (150 kD) inhibiting blood clearance and retarding accumulation of the radiopharmaceutical at the tumor site(s) (Maziere et al. (1986) *Exp Cell Res*, 167: 257–261).

SUMMARY OF THE INVENTION

This invention pertains to novel antibodies that specifically bind to the MUC-1 antigen. Certain preferred single-chain antibodies of this invention, designated as 12E, 3D, A5, C4, B5, E1, and B9 are shown in Table 2 (SEQ ID NOs:15–21). In addition, the VH and/or VL domains comprising these antibodies are illustrated in Table 1 (SEQ ID NOs:1–14). The VH and VL domains illustrated herein largely govern the specificity and binding affinity of the antibodies of this invention and permit the construction of a variety of antibodies that specifically target the MUC-1 antigen and cells bearing/displaying such an antigen.

Thus, in one embodiment, this invention provides an antibody that specifically binds MUC-1. The antibody preferably comprises a domain having the amino acid sequence of a polypeptide selected from the group consisting of a 12E variable light domain, a 3D variable light domain, an A5 variable light domain, a C4 variable light domain, a B5 variable light domain, an E1 variable light domain, a B9 variable light domain, a 12E variable heavy domain, a 3D variable heavy domain, an A5 variable heavy domain, a C4 variable heavy domain, a B5 variable heavy domain, an E1 variable heavy domain, and a B9 variable heavy domain. In certain embodiments, the antibody is a single chain (e.g. scFv) antibody. In certain embodiments the antibody is a multi-chain antibody, and/or a diabody, and/or a multivalent antibody. Particularly preferred antibodies of this invention comprise a variable light domain selected from the group consisting of a 12E variable light domain, a 3D variable light domain, an A5 variable light domain, a C4 variable light domain, a B5 variable light domain, an E1 variable light domain, and a B9 variable light domain, and a variable heavy domain selected from the group consisting of a 12E variable heavy domain, a 3D variable heavy domain, an A5 variable heavy domain, a C4 variable heavy domain, a B5 variable heavy domain, an E1 variable heavy domain, and a B9 variable heavy domain. Certain preferred antibodies include an antibody comprising a 12E variable heavy domain and a 12E variable light domain, an antibody comprising a 3D variable heavy domain and a 3D variable light domain, an antibody comprising an A5 variable heavy domain and an A5 variable light domain, an antibody comprising a C4 variable heavy domain and a C4 variable light domain, an antibody comprising a B5 variable heavy domain and a B5 variable light domain, an antibody comprising an E1 variable heavy domain and an E1 variable light domain, and an antibody comprising a B9 variable heavy domain and a B9 variable light domain.

In another embodiment, this invention provides a nucleic acid that encodes an antibody that specifically binds MUC-1, said nucleic acid comprising a nucleotide sequence encoding an amino acid sequence selected from the group consisting of a 12E variable light domain, a 3D variable light domain, an A5 variable light domain, a C4 variable light domain, a B5 variable light domain, an E1 variable light domain, a B9 variable light domain, a 12E variable heavy domain, a 3D variable heavy domain, an A5 variable heavy domain, a B5 variable heavy domain, an E1 variable heavy domain, and a B9 variable heavy domain. Preferred nucleic acids encodes a variable light domain selected from the group consisting of 12E variable light domain, a 3D variable light domain, an A5 variable light domain, a C4 variable light domain, a B5 variable light domain, an E1 variable light domain, and a B9 variable light domain, and a variable heavy domain selected from the group consisting of a 12E variable heavy domain, a 3D variable heavy domain, an A5 variable heavy domain, a C4 variable heavy domain, a B5 variable heavy domain, a an E1 variable heavy domain, and a B9 variable heavy domain. Certain preferred nucleic acids encode 12E variable heavy domain and a 12E variable light domain, a 3D variable heavy domain and a 3D variable light domain, an A5 variable heavy domain and an A5 variable light domain, a C4 variable heavy domain and a C4 variable light domain, a B5 variable heavy domain and a B5 variable light domain, an E1 variable heavy domain and an E1 variable light domain, and/or a B9 variable heavy domain and a B9 variable light domain. Particularly preferred nucleic acids encode a single chain (e.g. scFv) antibody of this invention and certain preferred nucleic acids are vectors.

In still another embodiment, this invention provides a chimeric molecule comprising an antibody attached to an effector, where the antibody is one of the antibodies described herein and the effector is selected from the group consisting of an epitope tag, a second antibody, a label, a cytotoxin, a liposome, a radionuclide, a drug, a prodrug, a liposome, and a chelate. In certain embodiments, the effector is an epitope tag (e.g. a biotin, avidin, streptavidin, etc.). In certain embodiments, the effector is a cytotoxin (e.g. *Diphtheria* toxin, *Pseudomonas* exotoxin, ricin, abrin, a thymidine kinase, etc.). In certain embodiments, the effector is a chelate comprising an isotope preferably a radioactive isotope. Particularly preferred isotopes include, but are not limited to gamma-emitters, positron-emitters, x-ray emitters and the like. Certain particularly preferred isotopes include, but are not limited to $^{99}$Tc, $^{203}$Pb, $^{67}$Ga, $^{68}$Ga, $^{72}$As, $^{111}$In, $^{113m}$In, $^{97}$Ru, $^{62}$Cu, $^{641}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag. In certain particularly preferred embodiments, the effector is a chelate comprising DOTA.

In still another embodiment, this invention provides methods of detecting a cell bearing a MUC-1 antigen (e.g. a cancer cell). The methods involve contacting a cell bearing a MUC-1 antigen with a chimeric molecule comprising an anti-MUC-1 antibody (e.g. as described herein) attached to an epitope tag (e.g. avidin, biotin, streptavidin, etc.), contacting the chimeric molecule with a chelate (e.g. DOTA) comprising a detectable moiety where the chelate binds to the epitope tag thereby associating the detectable moiety with the chelate; and detecting the detectable moiety. Preferred detectable moieties include radionucleides. Particularly preferred detectable moieties include, but are not limited to, a gamma-emitter, a positron-emitter, an x-ray emitters and fluorescence-emitters. Preferred detectable moieties include, but are not limited to $^{99}$Tc, $^{203}$Pb, $^{67}$Ga, $^{68}$Ga, $^{7272}$As, $^{111}$In, $^{113m}$In, $^{97}$Ru, $^{62}$Cu, $^{641}$Cu, $^{52}$Fe, $^{52m}$Mn, $^{51}$Cr, $^{186}$, Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag. In some embodiments, the detecting comprises external imaging. In certain embodiments, the detecting comprises internal imaging.

This invention also provides a method of detecting a cell bearing a MUC-1 antigen, where the method involves contacting a cell bearing a MUC-1 antigen with a chimeric molecule comprising an anti-MUC-1 antibody attached to a detectable label; and detecting the detectable label. Detectable labels include, but are not limited to the detectable labels described herein.

In still another embodiment, this invention provides a method of inhibiting growth or proliferation of a cell (e.g. a cancer cell) bearing a MUC-1 antigen. The method preferably involves contacting the cell bearing a MUC-1 antigen with a chimeric molecule comprising an anti-MUC-1 antibody (e.g. 12E, 3D, A5, C4, and variants thereof) attached to an effector selected from the group consisting of a cytotoxin, a radionuclide, a liposome comprising an anti-cancer drug, a prodrug, and an anti-cancer drug.

This invention also provides an antibody that specifically binds MUC-1 at an epitope specifically bound by a single-chain antibody selected from the group consisting of 12E, 3D, A5, and C4.

In still yet another embodiment, this invention provides an antibody that specifically binds MUC-1 at an epitope specifically bound by a single-chain antibody where the antibody comprises the amino acid sequence of a variable heavy chain and a variable light chain of an antibody selected from the group consisting of 12E, 3D, A5, C4, B5, E1, and B9, or conservative substitutions thereto.

In other embodiments, this invention provides various kits for practicing the methods described herein. Preferred kits comprise container containing an anti-MUC-1 antibody of this invention. Kits, optionally, further include an effector (e.g. an effector comprising a chelate). The effector and/or antibody can be provided in a pharmacologically acceptable excipient.

DEFINITIONS

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10): 1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature*, 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp169–176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The term "biotin" refers to biotin and modified biotins or biotin analogues that are capable of binding avidin or various avidin analogues. "Biotin", can be, inter alia, modified by the addition of one or more addends, usually through its free carboxyl residue. Useful biotin derivatives include, but are not limited to, active esters, amines, hydrazides and thiol groups that are coupled with a complimentary reactive group such as an amine, an acyl or alkyl group, a carbonyl group, an alkyl halide or a Michael-type acceptor on the appended compound or polymer.

Avidin, typically found in egg whites, has a very high binding affinity for biotin, which is a B-complex vitamin (Wilcheck et al. (1988) *Anal. Biochem*, 171: 1). Streptavidin, derived from *Streptomyces avidinii*, is similar to avidin, but has lower non-specific tissue binding, and therefore often is used in place of avidin. As used herein "avidin" includes all of its biological forms either in their natural states or in their modified forms. Modified forms of avidin which have been treated to remove the protein's carbohydrate residues ("deglycosylated avidin"), and/or its highly basic charge ("neutral avidin"), for example, also are useful in the invention. Both avidin and streptavidin have a tetravalency for biotin, thus permitting amplification when the former bind to biotin. In certain embodiments, four detection or therapeutic agents, such as nuclides, can be attached to each targeting protein.

The term "residue" as used herein refers to natural, synthetic, or modified amino acids.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The F(ab)'$_2$ may be reduced under mild conditions to break the disulfide linkage in the hinge region thereby converting the (Fab')$_2$ dimer into a Fab' monomer. The Fab' monomer is essentially a Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston, et al. (1988) *Proc. Nat. Acad. Sci. USA*, 85: 5879–5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p (see, e.g., U.S. Pat. No: 5733743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Particularly preferred antibodies should include all that have been displayed on phage (e.g., scFv, Fv, Fab and disulfide linked Fv (Reiter et al. (1995) *Protein Eng.* 8: 1323–1331).

The term "specifically binds", as used herein, when referring to a biomolecule (e.g., protein, nucleic acid, antibody, etc.), refers to a binding reaction that is determinative of the presence biomolecule in heterogeneous population of molecules (e.g., proteins and other biologics). Thus, under designated conditions (e.g. immunoassay conditions in the case of an antibody or stringent hybridization conditions in the case of a nucleic acid), the specified ligand or antibody binds to its particular "target" molecule and does not bind in a significant amount to other molecules present in the sample.

An "effector" refers to any molecule or combination of molecules whose activity it is desired to deliver/into and/or localize at cell. Effectors include, but are not limited to labels, cytotoxins, enzymes, growth factors, transcription factors, drugs, etc.

A "reporter" is an effector that provides a detectable signal (e.g. is a detectable label). In certain embodiments, the reporter need not provide the detectable signal itself, but can simply provide a moiety that subsequently can bind to a detectable label.

The term "conservative substitution" is used in reference to proteins or peptides to reflect amino acid substitutions that do not substantially alter the activity (specificity or binding affinity) of the molecule. Typically, conservative amino acid substitutions involve substitution of one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

The terms "epitope tag" or "affinity tag" are used interchangeably herein, and used refers to a molecule or domain of a molecule that is specifically recognized by an antibody or other binding partner. The term also refers to the binding partner complex as well. Thus, for example, biotin or a biotin/avidin complex are both regarded as an affinity tag. In addition to epitopes recognized in epitope/antibody interactions, affinity tags also comprise "epitopes" recognized by other binding molecules (e.g. ligands bound by receptors), ligands bound by other ligands to form heterodimers or homodimers, His$_6$ bound by Ni—NTA, biotin bound by avidin, streptavidin, or anti-biotin antibodies, and the like.

Epitope tags are well known to those of skill in the art. Moreover, antibodies specific to a wide variety of epitope tags are commercially available. These include but are not limited to antibodies against the DYKDDDDK (SEQ ID NO:9) epitope, c-myc antibodies (available from Sigma, St. Louis), the HNK-1 carbohydrate epitope, the HA epitope, the HSV epitope, the His$_4$, His$_5$, and HiS$_6$ epitopes that are recognized by the His epitope specific antibodies (see, e.g., Qiagen), and the like. In addition, vectors for epitope tagging proteins are commercially available. Thus, for example, the pCMV-Tag1 vector is an epitope tagging vector designed for gene expression in mammalian cells. A target gene inserted into the pCMV-Tag1 vector can be tagged with the FLAG ® epitope (N-terminal, C-terminal or internal tagging), the c-myc epitope (C-terminal) or both the FLAG (N-terminal) and c-myc (C-terminal) epitopes.

and Panel D: Anti-MUC-1 scFv is minimally-reactive with the Raji B-cell lymphoma cells.

Figure 4:
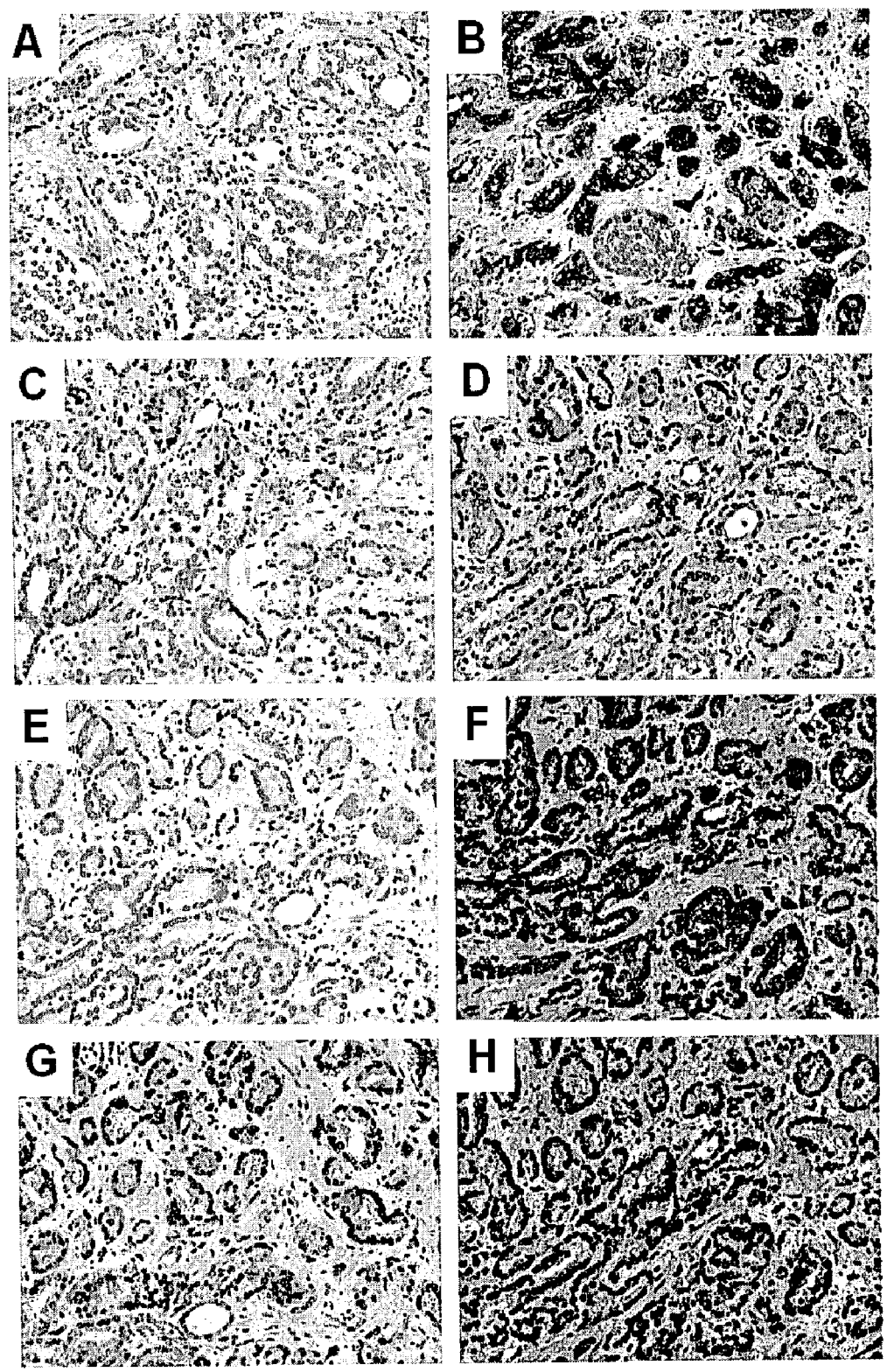

FIG. 4, panels A through H, illustrates staining of prostate cancer using three of the scFv described herein. Panel A: negative control Mab stain; Panel B: antiMuc-1 monoclonal Ab (BrE3)(as positive control for MUC-1); Panel C: C=12E scFv; Panel D: 12E scFv diabody; Panel E: E scFv; Panel F: E1 scFv diabody; Panel G: G1(B5) scFV; and Panel H: G (B5) scFv diabody.

DETAILED DESCRIPTION

This invention pertains to the identification of antibodies that specifically bind to one of the epithelial mucin family of molecules; MUC-1. MUC-1 is widely expressed on a large number of epithelial cancers and is aberrantly glycosylated making it structurally and antigenically distinct from that expressed by non-malignant cells (Barratt-Boyes (1996) *Cancer Immunol Immunother*,43: 142–151; Price et al. (1998) *Tumor Biology*, 19:1–20; Peterson et al. (1991), Pages 55–68 In: Breast Epithelial Antigens, R. L. Ceriani. (ed.), New York: Plenum Press). In normal epithelial tissue, MUC-1 is localized to the apical region of the cells; malignant transformation results in upregulation of MUC-1 by gene amplification and/or increased transcriptional activation and the distribution of MUC-1 on the cell surface is no longer confined to the apical region (Bieche, and Lidereau (1997) *Cancer Genetics and Cytogenetics*, 98: 75–80). While the function of MUC-1 still awaits clarification, high cytoplasmic expression of MUC-1 has been associated with poor prognosis in patients with breast and/or ovarian cancers.

Because MUC-1 is upregulated on cancer cells, and is also "abnormally" glycosylated (and therefore antigenically distinct), MUC-1 provides a good cancer specific marker that can act as a convenient target for specifically delivering various effectors (e.g. cytotoxins, labels, drugs or prodrugs, and the like) to cancer cells and/or to cells adjacent to cancer cells.

The anti-MUC 1 antibodies of this invention thus provide effective targeting moieties (i.e. moieties that specifically bind to a target such as MUC 1 displayed on a cell) that can be transiently or permanently coupled to an effector (thereby forming a chimeric molecule or chimeric moiety) and used to direct that effector to a particular target cell (e.g. a cancer cell) expressing MUC 1. The antibodies of this invention are particularly advantageous in this respect. Because of their small size they show reduced immunogenicity and improved tumor penetration. In addition the antibodies of this invention show high binding affinity for MUC 1 positive cancer cells. In addition, the single-chain antibodies of this invention are easily produced using a cost-effective bacterial expression system providing, e.g. 600–800 μg of soluble protein per liter of bacterial culture even in the suboptimal production method of shaker flasks.

The various effectors (e.g. cytotoxins, labels, therapeutic agents, etc.) can be targeted to in vivo target sites, such as neoplastic cells, solid tumors, metastatic cells and the like, using targeting or "pretargeting" protocols. Targeting protocols utilize a chimeric molecule comprising an effector that bears the desired activity (e.g. cytotoxicity, radioactivity, etc.) it is desired to deliver to the target site. Binding of the chimeric molecule to the target effectively delivers the desired activity.

In pretargeting protocols, a chimeric molecule is utilized comprising a primary targeting species (e.g. an anti MUC 1 antibody) that specifically binds the desired target (e.g. a cancer cell) and an effector that provides a binding site that is available for binding by a subsequently administered second targeting species. Once sufficient accretion of the primary targeting species (the chimeric molecule) is achieved, a second targeting species comprising (i) a diagnostic or therapeutic agent and (ii) a second targeting moiety, that recognizes the available binding site of the primary targeting species, is administered.

An illustrative example of a pretargeting protocol is the biotin-avidin system for administering a cytotoxic radionuclide to a tumor. In a typical procedure, a monoclonal antibody (e.g. anti-MUC 1) targeted against a tumor-associated antigen is conjugated to avidin and administered to a patient who has a tumor recognized by the antibody. Then the therapeutic agent, e.g., a chelated radionuclide covalently bound to biotin, is administered. The radionuclide, via its attached biotin is taken up by the antibody-avidin conjugate pretargeted at the tumor. Examples of pre-targeting biotin/avidin protocols are described, for example, in Goodwin et al., U.S. Pat. No. 4,863,713; Goodwin et al. (1988) *J. Nucl. Med.* 29: 226; Hnatowich et al. (1987) *J. Nucl. Med.* 28: 1294; Oehr et al. (1988) *J. Nucl. Med.* 29: 728; Klibanov et al. (1988) *J. Nucl. Med.* 29: 1951; Sinitsyn et al. (1989) *J. Nucl. Med.* 30: 66; Kalofonos et al. (1990) *J. Nucl. Med.* 31: 1791; Schechter et al. (1991) *Int. J. Cancer* 48:167; Paganelli etal. (1991) *Cancer Res.* 51: 5960; Paganelli et al. (1991) *Nucl. Med. Commun.* 12: 211; Stickney et al. (1991) *Cancer Res.* 51: 6650; and Yuan et al. (1991) *Cancer Res.* 51:3119.

Three-step pretargeting protocols in which a clearing agent is administered after the first targeting composition has localized at the target site also have been described. The clearing agent binds and removes circulating primary conjugate which is not bound at the target site, and prevents circulating primary targeting species (antibody-avidin or conjugate, for example) from interfering with the targeting of active agent species (biotin-active agent conjugate) at the target site by competing for the binding sites on the active agent-conjugate. When antibody-avidin is used as the primary targeting moiety, excess circulating conjugate can be cleared by injecting a biotinylated polymer such as biotinylated human serum albumin. This type of agent forms a high molecular weight species with the circulating avidin-antibody conjugate which is quickly recognized by the hepatobiliary system and deposited primarily in the liver.

Examples of these protocols are disclosed, e.g., in PCT Application No. WO 93/25240; Paganelli et al. (1991) *Nucl. Med. Comm.*, 12: 211–234; Oehr et al. (1988) *J. Nucl. Med.*, 29: 728–729; Kalofonos et al. (1990) *J. Nucl. Med.*, 31: 1791–1796; Goodwin et al. (1988) *J. Nucl. Med.*, 29: 226–234. Improved pretargeting protocols using the biotin-avidin system are disclosed, e.g., in U.S. Pat. Nos. 5,525, 338, 5,482,698, and the like.

I. Anti-MUC-1 Antibodies.

In certain embodiments, this invention provides anti-MUC-1 antibodies that specifically bind to one of the epithelial mucin family of molecules; MUC-1. MUC-1 is widely expressed on a large number of epithelial cancers and is aberrantly glycosylated making it structurally and antigenically distinct from that expressed by non-malignant cells the antibodies of this invention are particularly useful for targeting various effectors (e.g. imaging reagents, cytotoxins, etc.) to cancer cells. It will be appreciated that such targeting need not be totally specific, but is of use if it provides even preferential delivery of the effector to the target (e.g. cancer) cell(s).

In certain embodiments, the antibodies of this invention comprise a variable heavy and/or a variable light chain derived from (or having the sequence of) a variable heavy and/or a variable light chain of one or more of the single chain antibodies designated herein as 12E, 3D, A5, C4, B5, E1, and B9 (see, e.g., Table 1).

TABLE 1

VH and VL domains of anti-MUC-1 antibodies.

| Antibody Domain | Amino Acid Sequence | SEQ ID NO |
|---|---|---|
| 12E V$_H$ | QVKLQQSGTE VVKPGASVKL SCKASGYIFT SYDIDWVRQT PEQGLEWIGW TFPGEGSTEY NEKFKGRATL SVDKSSSTAY MELTRLTSED SAVYFCARGD YYRRYFDLWG QGTTVTVSS | 1 |
| 12E V$_L$ | DIELTQSPAI MSASPGERVT MTCSASSSIR YIYWYQQKPG SSPRLLIYDT SNVAPGVPFR FSGSGSGTSY SLTINRMEAE DAATYYCQEW SGYPYTFGGG TKLELKRAAA | 2 |
| 3D V$_H$ | QVKLQESGPE VVKPGASVKL SCKASGYIFT SYDIDWVRQT PEQGLEWIGW IFPGEGSTEY NEKFKGRATL SVDKSSSTAY MELTRLTSED SAVYFCARGD YYRRYFDLWG QGTTVTVSS | 3 |
| 3D V$_L$ | DIELTQSPGV KTGTKLELKR AAA | 4 |
| A5 V$_H$ | QVKLQQSGPG LCSPHEACPS PAQPLVSHLL MVYTGFASLQ ERVWSGWEYG VVEAQTIIQL SYPDTSTRTT PRAKFSLKWT VYNLMTEAYT TVGVMGTSLT PGANGTTVTV SS | 5 |
| A5 V$_L$ | DTSSLSLQLP LYLWGRGPPS HTGPAKVSVH LAIVICTGTN RNQDSHPDSS SILYPTIWGP CQVQWQWVWD RLHPQHPSCG GRGCLQPITV STLGAYTFGG GTKLELKRAA A | 6 |
| C4 V$_H$ | QVQLQESGPG LVQPSQSLST TCTVSGFSLT AYGVHWTRQS PGKGLEWLGV IWSGGGTDYN PAFISRLNIN KDNSKSQVFF KVDSLQLDDR GIYYCVRRNG YFFDSWGQGT TVTVSS | 7 |
| C4 V$_L$ | DIELTQSPAS LLCLWGRGPP SHAGPTNVVS TSGYNFIYWS QQKPGQSPKL LIYLSSNLES GVPARVSGSG SRTYFTLNIH PVEEEDAATF YCRHTRELPC TFGGRTKLEI KRAAAGAPVP YPDPLEPPAA | 8 |
| B5 V$_H$ | QVKLQESG AELVRPGASV TLSCKASGYT FTDYEMHWVK QTPVHGLEWI GAIDPETGGT AYNQKFKGKA TLTADKSSST AYMELRSLTS EDSAVYYCTR DGYYAWFAYW GQGTTVTVSS | 9 |
| B5 V$_L$ | DIELT QSPAIMSASP GERVTMTCSA SSSIRYIYWY QQKPGSSPRL LIYDTSNVAP GVPFRFSGSG SGTSYSLTIN RMEAEDAATY YCQEWSGYPY TFGGGTKLEL KRAAA | 10 |
| E1 V$_H$ | QVKLQQSC AELVRPGASV KLSCKASGYT FTSYWMNWVK QRPGQGLEWI GMIDPSDSET HYNQMFKDKA TLTVDKSSST AYMQLSSLTS EDSAVYYCAR DGSSSWFAYW GQGTTVTVSS | 11 |
| E1 V$_L$ | DIELT QSPAIMSASP GERVTMTCSA SSSIRYIYWY QQKPGSSPRL LIYDTSNVAP GVPFRFSGSG SGTSYSLTIN RMEAEDAATY YCQEWSGYPY TFGGGTKLEI KPAAA | 12 |
| B9 V$_H$ | QVKLQESG AELVRPGASV KLSCKASGYS FTSYWMNWVK QRPGQGLEWI GMIHPSDSET HYNQMFKDKA TLTVDKSSST AYMQLSSLTS EDSAVYYCAR DGSSSWFAYW GQGTTVTVSS | 13 |
| B9 V$_L$ | DIELT QSPIGQVGNK TGPKLEIKRA AA | 14 |

In certain embodiments the variable light and variable heavy chain domains are joined by a peptide linker (e.g. Gly$_4$(Ser)$_3$ (SEQ ID NO:22) to form a single-chain antibodies Illustrative sequences of such single-chain antibodies are illustrated in Table 2.

TABLE 2

Anti-MUC-1 single-chain antibodies.

| Antibody Domain | Amino Acid Sequence | SEQ ID NO |
|---|---|---|
| 12E | VKKLLFAIPL VVPFYAAQPA MAQVKLQQSG TEVVKPGASV KLSCKASGYI FTSYDIDWVR QTPEQGLEWI GWIFPGEGST EYNEKFKGRA TLSVDKSSST AYMELTRLTS EDSAVYFCAR GDYYRRYFDL WGQGTTVTVS SRGGGSGGGG SGGGGSDIEL TQSPAIMSAS PGERVTMTCS ASSSIRYIYW YQQKPGSSPR | 15 |

TABLE 2-continued

Anti-MUC-1 single-chain antibodies.

| Antibody Domain | Amino Acid Sequence | SEQ ID NO |
|---|---|---|
|  | LLIYDTSNVA PGVPFRFSGS GSGTSYSLTI NRMEAEDAAT<br>YYCQEWSGYP YTFCGGTKLE LKRAAAGAPV PYPDPLEPRA A |  |
| 3D | VKKLLFAIPL VVPFYAAQPA MAQVKLQESG PEVVKPGASV<br>KLSCKASGYI FTSYDIDWVR QTPEQGLEWI GWIFPGEGST<br>EYNEKFKGRA TLSVDKSSST AYMELTRLTS EDSAVYFCAR<br>GDYYRRYFDL WGQGTTVTVS SGGGGSGGGG SGGGGSDIEL<br>TQSPGVKTGT KLELKRAAAG APVPYPDPLE PRAA | 16 |
| A5 | VKKLLFATPL VVPFYAAQPA MAQVKLQQSG PGLCSPHRAC<br>PSPAQPLVSH *LLMVYIGFA SLQERVWSGW E*YGVVEAQT<br>IIQLSYPD*T STRTTPRAKF SLKWTVYNLM TEAYTTV*GV<br>MGTSLTPGAN GTTVTVSSGG GGSGGGSGG GGSDISSLSL<br>QLP*LYLWGR GPPSHTGPAK VSVHLAIVIC TGTNRNQDSH<br>PDSSSILYPT*IWGPCQVQWQ WVWDRLHPQH PSCGGRGCLQ<br>PITVSTLGAY TFGGGTKLEL KRAAAGAPVP YPDPLEPPAA | 17 |
| C4 | QVQLQESGPC LVQPSQSLSI TCTVSGFSLT AYCVHWIRQS<br>PGKGLEWLGV TWSGGGTDYN PAFISRLNIN KDNSKSQVFF<br>KVDSLQLDDR GIYYCVRRNG YFFDSWGQGT TVTVSSSGRF<br>SGGGSGGGGS DIELTQSPAS LLCLWGRGPP SHAGPTMVVS<br>TSGYNFIYWS QQKPGQSPKL LIYLSSNLES GVPARVSGSG<br>SRTYFTLNIH PVEEEDAATF YCRHTRELPC TFGGRTKLEI<br>KRAAAGAPVP YPDPLEPRAA | 18 |
| B5 | NAQVKLQESG AELVRPGASV TLSCKASGYT FTDYEMHWVK<br>QTPVHGLEWI GAIDPETGGT AYNQKFKGKA TLTADKSSST<br>AYMELRSLTS EDSAVYYCTR DGYYAWFAYW GQGTTVTVSS<br>GGGGLGGGGS GGGGSDIELT QSPAIMSASP GERVTMTCSA<br>SSSIRYIYWY QQKPGSSPRL LIYDTSNVAP GVPFRFSGSG<br>SGTSYSLTIN RMEAEDAATY YCQEWSGYPY TFGGGTKLEL<br>KRAAAGAPVP YPDPLEPRAA* | 19 |
| E1 | MAQVKLQQSG AELVRPGASV KLSCKASGYT FTSYWHNWVK<br>QRPGQGLEWI GMIDPSDSET HYNQMFKDKA TLTVDKSSST<br>AYMQLSSLTS EDSAVYYCAR DGSSSWFAYW GQGTTVTVSS<br>GGGGSGGGGS GGGGSDIELT QSPAIMSASP GERVTMTCSA<br>SSSIRYIYWY QQKPGSSPRL LIYDTSNVAP GVPFRFSGSG<br>SGTSYSLTIN RMEAEDAATY YCQEWSGYPY TFGGGTKLEI<br>KRAAAGAPVP YPDPLEPRAA* | 20 |
| B9 | MAQVKLQESG AELVRPGASV KLSCKASGYS FTSYWMNWVK<br>QRPGQGLEWI GMIHPSDSET HYNQMFKDKA TLTVDKSSST<br>AYMQLSSLTS EDSAVYYCAR DGSSSWFAYW GQGTTVTVSS<br>GGGGSGGGGS GGGCSDIELT QSPIGQVGNK TGPKLEIKRA<br>AAGAPVPYPD PLEPRAA* | 21 |

II. Chimeric Moieties Comprising Anti-MUC-1 Antibodies.

Since MUC-1 is found in upregulated in cancer cells, anti-MUC-1, it can be exploited as target for the efficient and specific delivery of an effector (e.g. an effector molecule such as a cytotoxin, a radiolabel, etc.) to various cancer cells (e.g. isolated cells, metastatic cells, solid tumor cells, etc.), particular to epithelial cancer cells (e.g. breast cancer cells). MUC-1 need not exist solely on cancer cells to provide an effective target. Differential expression of MUC-1 on cancer cells, as compared to healthy cells, is sufficient to provide significant and useful targeting advantage, i.e. resulting in preferential delivery of the effector moiety to the target (e.g. cancer) cell.

In preferred embodiments, the anti-MUC-1 antibodies of this invention are utilized in a "pretargeting" strategy (resulting in formation of a chimeric moiety at the target site after administration of the effector moiety) or in a "targeting" strategy where the anti-MUC-1 antibody is coupled to an effector molecule prior to use to provide a chimeric molecule.

A chimeric molecule or chimeric composition or chimeric moiety refers to a molecule or composition wherein two or more molecules that exist separately in their native state are joined together to form a single molecule having the desired functionality of its constituent molecules. Typically, one of the constituent molecules of a chimeric molecule is a "targeting molecule". The targeting molecule is a molecule such as a ligand or an antibody that specifically binds to its corresponding target, in this case MUC-1.

Another constituent of the chimeric molecule is an "effector". The effector molecule refers to a molecule or group of molecules that is to be specifically transported to the target cell (e.g., a cell expressing MUC-1). The effector molecule typically has a characteristic activity that is to be delivered to the target cell. Effector molecules include, but are not limited to cytotoxins, labels, radionuclides, ligands, antibodies, drugs, liposomes, and the like.

In certain embodiments, the effector is a detectable label, with preferred detectable labels including radionuclides. Among the radionuclides and labels useful in the radionuclide-chelator-(e.g. biotin) conjugates of the present invention, gamma-emitters, positron-emitters, x-ray emitters and fluorescence-emitters are suitable for localization, diagnosis and/or staging, and/or therapy, while beta and alpha-emitters and electron and neutron-capturing agents, such as boron and uranium, also can be used for therapy.

The detectable labels can be used in conjunction with an external detector and/or an internal detector and provide a means of effectively localizing and/or visualizing cells bearing MUC-1 antigen (e.g. cancer cells, solid tumors, etc.). Such detection/visualization can be useful in various contexts including, but not limited to pre-operative and intraoperative settings. Thus, in certain embodiment this invention relates to a method of intraoperatively detecting and locating tissues having MUC-1 markers in the body of a mammal. These methods typically involve administering to the mammal a composition comprising, in a quantity sufficient for detection by a detector (e.g. a gamma detecting probe), an anti-MUC-1 labeled with a detectable label (e.g. anti-MUC-1 antibodies of this invention labeled with a radioisotope, e.g. $^{161}$Tb, $^{123}$I, $^{125}$I, and the like), and, after allowing the active substance to be taken up by the target tissue, and preferably after blood clearance of the label, subjecting the mammal to a radioimmunodetection technique in the relevant area of the body, e.g. by using a gamma detecting probe.

The label-bound anti-MUC-1 antibody can be used in the technique of radioguided surgery, wherein relevant tissues in the body of a subject can be detected and located intraoperatively by means of a detector, e.g. a gamma detecting probe. The surgeon can, intraoperatively, use this probe to find the tissues in which uptake of the compound labeled with a radioisotope, that is, e.g. a low-energy gamma photon emitter, has taken place.

In addition to detectable labels, preferred effectors include cytotoxins (e.g. *Pseudomonas* exotoxin, ricin, abrin, *Diphtheria* toxin, and the like), or cytotoxic drugs or prodrugs, in which case the chimeric molecule may act as a potent cell-killing agent specifically targeting the cytotoxin to cells bearing the MUC-1 target.

In still other embodiments, the effector can include a liposome encapsulating a drug (e.g. an anti-cancer drug such as doxirubicin, vinblastine, taxol, etc.), an antigen that stimulates recognition of the bound cell by components of the immune system, and antibody that specifically binds immune system components and directs them to the MUC-1 bearing cell, and the like.

A) The Anti-MUC-1 Targeting Molecule.

In preferred embodiments, of the methods and compositions of this invention, the targeting molecule is an antibody that specifically binds to a MUC-1 antigen. The antibody can be a full-length antibody polyclonal or monoclonal antibody, an antibody fragment (e.g. Fv, Fab, etc.), or a single chain antibody (e.g. scFv). Particularly preferred antibodies include 12E, 3D, A5, and variants thereof as described herein.

The antibody can be produced according to standard methods well known to those of skill in the art as described below. The antibody once produced can be chemically conjugated to the effector.

Where one of the effector molecule(s) is a protein, the antibody can be a single chain antibody and the chimeric molecule can be a recombinantly expressed fusion protein. Means of producing such recombinant fusion proteins are well known to those of skill in the art.

B) Certain Preferred Effectors.

1) Imaging Compositions.

In certain embodiments, the chimeric molecules of this invention can be used to direct detectable labels to a tumor site. This can facilitate tumor detection and/or localization. In certain particularly preferred embodiments, the effector component of the chimeric molecule is a "radioopaque" label, e.g. a label that can be easily visualized using x-rays. Radioopaque materials are well known to those of skill in the art. The most common radiopaque materials include iodide, bromide or barium salts. Other radiopaque materials are also known and include, but are not limited to organic bismuth derivatives (see, e.g., U.S. Pat. No. 5,939,045), radiopaque polyurethanes (see U.S. Pat. No. 5,346,981, organobismuth composites (see, e.g., U.S. Pat. No. 5,256,334), radiopaque barium polymer complexes (see, e.g., U.S. Pat. No. 4,866,132), and the like.

The anti-MUC-1 antibody(s) can be coupled directly to the radiopaque moiety or they can be attached to a "package" (e.g. a chelate, a liposome, a polymer microbead, etc.) carrying or containing the radiopaque material as described below.

In addition to radioopaque labels, other labels are also suitable for use in this invention. Detectable labels suitable for use as the effector molecule component of the chimeric molecules of this invention include any composition detectable by spectroscopic, photochemical, biochemical, immunochemical, electrical, optical or chemical means. Useful labels in the present invention include magnetic beads (e.g. DYNABEADS™), fluorescent dyes (e.g., fluorescein isothiocyanate, texas red, rhodamine, green fluorescent protein, and the like), radiolabels (e.g., $^{3}$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

Various preferred radiolabels include, but are not limited to $^{99}$Tc, $^{203}$Pb, $^{67}$Ga, $^{68}$Ga, $^{72}$As, $^{111}$In, $^{113m}$In, $^{97}$Ru, $^{62}$Cu, $^{641}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag.

Means of detecting such labels are well known to those of skill in the art. Thus, for example, radiolabels may be detected using photographic film, scintillation detectors, and the like. Fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

2) Radiosensitizers

In another embodiment, the effector can be a radiosensitizer that enhances the cytotoxic effect of ionizing radiation (e.g., such as might be produced by $^{60}$Co or an x-ray source) on a cell. Numerous radiosensitizing agents are known and include, but are not limited to benzoporphyrin derivative compounds (see, e.g., U.S. Pat. No. 5,945,439), 1,2,4-benzotriazine oxides (see, e.g., U.S. Pat. No. 5,849,738), compounds containing certain diamines (see, e.g., U.S. Pat. No. 5,700,825), BCNT (see, e.g., U.S. Pat. No. 5,872,107), radiosensitizing nitrobenzoic acid amide derivatives (see, e.g., U.S. Pat. No. 4,474,814), various heterocyclic derivatives (see, e.g., U.S. Pat. No. 5,064,849), platinum complexes (see, e.g., U.S. Pat. No. 4,921,963), and the like.

3) Ligands

The effector molecule may also be a ligand, and epitope tag, or an antibody. Particularly preferred ligand and antibodies are those that bind to surface markers on immune cells. Chimeric molecules utilizing such antibodies as effector molecules act as bifunctional linkers establishing an association between the immune cells bearing binding partner for the ligand or antibody and the tumor cells expressing the MUC-1 antigen.

3) Chelates

Many of the pharmaceuticals and/or radiolabels described herein are preferably provided as a chelate, particularly where a pre-targeting strategy is utilized. The chelating molecule is typically coupled to a molecule (e.g. biotin, avidin, streptavidin, etc.) that specifically binds an epitope tag attached to the anti-MUC-1 antibody.

Chelating groups are well known to those of skill in the art. In certain embodiments, chelating groups are derived from ethylene diamine tetra-acetic acid (EDTA), diethylene triamine penta-acetic acid (DTPA), cyclohexyl 1,2-diamine tetra-acetic acid (CDTA), ethyleneglycol-O,O'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N'-,N''',N''''-tetra-acetic acid (DOTA), hydroxyethyldiamine triacetic acid (HEDTA), 1,4,8,11-tetra-azacyclotetradecane-N,N', N',N''''-tetra-acetic acid (TETA), substituted DTPA, substituted EDTA, and the like.

Examples of certain preferred chelators include unsubstituted or, substituted 2-iminothiolanes and 2-iminothiacyclohexanes, in particular 2-imino-4-mercaptomethylthiolane.

One chelating agent, 1,4,7,10-tetraazacyclododecane-N, N, N', N'''-tetraacetic acid (DOTA), is of particular interest because of its ability to chelate a number of diagnostically and therapeutically important metals, such as radionuclides and radiolabels.

Conjugates of DOTA and proteins such as antibodies have been described. For example, U.S. Pat. No. 5,428,156 teaches a method for conjugating DOTA to antibodies and antibody fragments. To make these conjugates, one carboxylic acid group of DOTA is converted to an active ester which can react with an amine or sulfhydryl group on the antibody or antibody fragment. Lewis et al. (1994) *Bioconjugate Chem.* 5: 565–576, describes a similar method wherein one carboxyl group of DOTA is converted to an active ester, and the activated DOTA is mixed with an antibody, linking the antibody to DOTA via the epsilon-amino group of a lysine residue of the antibody, thereby converting one carboxyl group of DOTA to an amide moiety.

Alternatively, the chelating agent can be coupled, directly or through a linker, to an epitope tag or to a moiety that binds an epitope tag. Conjugates of DOTA and biotin have been described (see, e.g., Su (1995) *J. Nucl. Med.*, 36 (5 Suppl): 154P, which discloses the linkage of DOTA to biotin via available amino side chain biotin derivatives such as DOTA-LC-biotin or DOTA-benzyl-4-(6-amino-caproamide)-biotin). Yau et al., WO 95/15335, disclose a method of producing nitro-benzyl-DOTA compounds that can be conjugated to biotin. The method comprises a cyclization reaction via transient projection of a hydroxy group; tosylation of an amine; deprotection of the transiently protected hydroxy group; tosylation of the deprotected hydroxy group; and intramolecular tosylate cyclization. Wu et al. (1992) *Nucl. Med. Biol.*, 19(2): 239–244 discloses a synthesis of macrocylic chelating agents for radiolabeling proteins with $^{111}$IN and $^{90}$Y. Wu et al. makes a labeled DOTA-biotin conjugate to study the stability and biodistribution of conjugates with avidin, a model protein for studies. This conjugate was made using a biotin hydrazide which contained a free amino group to react with an in situ generated activated DOTA derivative.

1) Cytotoxins

Particularly preferred cytotoxins include *Pseudomonas* exotoxins, *Diphtheria* toxins, ricin, and abrin. *Pseudomonas* exotoxin and *Dipthteria* toxin are most preferred.

*Pseudomonas* exotoxin A (PE) is an extremely active monomeric protein (molecular weight 66 kD), secreted by *Pseudomonas aeruginosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain Ia (amino acids 1–252) mediates cell binding. Domain II (amino acids 253–364) is responsible for translocation into the cytosol and domain III (amino acids 400–613) mediates ADP ribosylation of elongation factor 2, which inactivates the protein and causes cell death. The function of domain Ib (amino acids 365–399) remains undefined, although a large part of it, amino acids 365–380, can be deleted without loss of cytotoxicity. See Siegall et al. (1989) *J. Biol. Chem.* 264: 14256–14261.

Where the targeting molecule (e.g. anti-MUC-1) is fused to PE, a preferred PE molecule is one in which domain Ia (amino acids 1 through 252) is deleted and amino acids 365 to 380 have been deleted from domain Ib. However all of domain Ib and a portion of domain II (amino acids 350 to 394) can be deleted, particularly if the deleted sequences are replaced with a linking peptide such as GGGGS (SEQ ID NO:10).

In addition, the PE molecules can be further modified using site-directed mutagenesis or other techniques known in the art, to alter the molecule for a particular desired application. Means to alter the PE molecule in a manner that does not substantially affect the functional advantages provided by the PE molecules described here can also be used and such resulting molecules are intended to be covered herein.

For maximum cytotoxic properties of a preferred PE molecule, several modifications to the molecule are recommended. An appropriate carboxyl terminal sequence to the recombinant molecule is preferred to translocate the molecule into the cytosol of target cells. Amino acid sequences which have been found to be effective include, REDLK (SEQ ID NO:11) (as in native PE), REDL (SEQ ID NO:12), RDEL (SEQ ID NO:13), or KDEL (SEQ ID NO:14), repeats of those, or other sequences that function to maintain or recycle proteins into the endoplasmic reticulum, referred to here as "endoplasmic retention sequences". See, for example, Chaudhary et al. (1991) *Proc. Natl. Acad. Sci. USA* 87:308–312 and Seetharam et al, *J. Biol. Chem.* 266: 17376–17381. Preferred forms of PE comprise the PE molecule designated PE38QQR. (Debinski et al. *Bioconj. Chem.*, 5: 40 (1994)), and PE4E (see, e.g., Chaudhary et al. (1995) *J. Biol. Chem.*, 265:16306).

Methods of cloning genes encoding PE fused to various ligands are well known to those of skill in the art (see, e.g., Siegall et al. (1989) *FASEB J.*, 3: 2647–2652; and Chaudhary et al. (1987) *Proc. Natl. Acad. Sci. USA*, 84: 4538–4542).

Like PE, diphtheria toxin (DT) kills cells by ADP-ribosylating elongation factor 2 thereby inhibiting protein synthesis. *Diphtheria* toxin, however, is divided into two chains, A and B, linked by a disulfide bridge. In contrast to PE, chain B of DT, which is on the carboxyl end, is responsible for receptor binding and chain A, which is present on the amino end, contains the enzymatic activity (Uchida et al.(1972) *Science*, 175: 901–903; Uchida et al. (1973) *J. Biol. Chem.*, 248: 3838–3844).

In a preferred embodiment, the targeting molecule-*Diphtheria* toxin fusion proteins of this invention have the native receptor-binding domain removed by truncation of the *Diphtheria* toxin B chain. Particularly preferred is DT388, a DT in which the carboxyl terminal sequence beginning at residue 389 is removed. Chaudhary et al. (1991) *Bioch. Biophys. Res. Comm.*, 180: 545–551. Like the PE chimeric cytotoxins, the DT molecules may be chemically conjugated to the MUC-1 antibody, but, in certain preferred embodiments, the targeting molecule will be fused to the *Diphtheria* toxin by recombinant means (see, e.g., Williams et al. (1990) *J. Biol. Chem.* 265: 11885–11889).

4) Other Therapeutic Moieties

Other suitable effector molecules include pharmacological agents or encapsulation systems containing various pharmacological agents. Thus, the targeting molecule of the chimeric molecule may be attached directly to a drug that is to be delivered directly to the tumor. Such drugs are well known to those of skill in the art and include, but are not limited to, doxirubicin, vinblastine, genistein, an antisense molecule, and the like.

Alternatively, the effector molecule may be an encapsulation system, such as a viral capsid, a liposome, or micelle that contains a therapeutic composition such as a drug, a nucleic acid (e.g. an antisense nucleic acid), or another therapeutic moiety that is preferably shielded from direct exposure to the circulatory system. Means of preparing liposomes attached to antibodies are well known to those of skill in the art. See, for example, U.S. Pat. No. 4,957,735, Connor et al. (1985) *Pham. Ther.*, 28: 341–365.

C) Attachment of the Targeting Molecule to the Effector Molecule.

One of skill will appreciate that the MUC-1 antibodies of this invention and the effector molecules may be joined together in any order. Thus, where the targeting molecule is a polypeptide, the effector molecule may be joined to either the amino or carboxy termini of the targeting molecule. The targeting molecule may also be joined to an internal region of the effector molecule, or conversely, the effector molecule may be joined to an internal location of the targeting molecule, as long as the attachment does not interfere with the respective activities of the molecules.

The targeting molecule and the effector molecule may be attached by any of a number of means well known to those of skill in the art. Typically the effector molecule is conjugated, either directly or through a linker (spacer), to the targeting molecule. However, where both the effector molecule and the targeting molecule are polypeptides it is preferable to recombinantly express the chimeric molecule as a single-chain fusion protein.

1) Conjugation of the Effector Molecule to the Targeting Molecule

In one embodiment, the targeting molecule (e.g., anti-MUC-1 Ab) is chemically conjugated to the effector molecule (e.g., a cytotoxin, a label, a ligand, or a drug or liposome). Means of chemically conjugating molecules are well known to those of skill.

The procedure for attaching an agent to an antibody or other polypeptide targeting molecule will vary according to the chemical structure of the agent. Polypeptides typically contain variety of functional groups; e.g., carboxylic acid (COOH) or free amine ($—NH_2$) groups, which are available for reaction with a suitable functional group on an effector molecule to bind the effector thereto.

Alternatively, the targeting molecule and/or effector molecule may be derivatized to expose or attach additional reactive functional groups. The derivatization may involve attachment of any of a number of linker molecules such as those available from Pierce Chemical Company, Rockford Ill.

A "linker", as used herein, is a molecule that is used to join the targeting molecule to the effector molecule. The linker is capable of forming covalent bonds to both the targeting molecule and to the effector molecule. Suitable linkers are well known to those of skill in the art and include, but are not limited to, straight or branched-chain carbon linkers, heterocyclic carbon linkers, or peptide linkers. Where the targeting molecule and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

A bifunctional linker having one functional group reactive with a group on a particular agent, and another group reactive with an antibody, may be used to form the desired immunoconjugate. Alternatively, derivatization may involve chemical treatment of the targeting molecule, e.g., glycol cleavage of the sugar moiety of a the glycoprotein antibody with periodate to generate free aldehyde groups. The free aldehyde groups on the antibody may be reacted with free amine or hydrazine groups on an agent to bind the agent thereto. (See U.S. Pat. No. 4,671,958). Procedures for generation of free sulfhydryl groups on polypeptide, such as antibodies or antibody fragments, are also known (See U.S. Pat. No. 4,659,839).

Many procedure and linker molecules for attachment of various compounds including radionuclide metal chelates, toxins and drugs to proteins such as antibodies are known (see, e.g., European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071–4075). In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine*, Academic Press, pp. 168–190 (1982), Waldmann (1991) *Science*, 252: 1657, U.S. Pat. Nos. 4,545,985 and 4,894,443.

In some circumstances, it is desirable to free the effector molecule from the targeting molecule when the chimeric molecule has reached its target site. Therefore, chimeric conjugates comprising linkages which are cleavable in the vicinity of the target site may be used when the effector is to be released at the target site. Cleaving of the linkage to release the agent from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis.

U.S. Pat. No. 4,671,958, for example, includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

2 Conjugation of Chelates

In certain preferred embodiments, the effector comprises a chelate that is attached to an antibody or to an epitope tag. The MUC-1 antibody bears a corresponding epitope tag or antibody so that simple contacting of the MUC-1 antibody to the chelate results in attachment of the antibody with the effector. The combining step can be performed before the moiety is used (targeting strategy) or the target tissue can be bound to the anti-MNC-1 antibody before the chelate is delivered. Methods of producing chelates suitable for coupling to various targeting moieties are well known to those of skill in the art (see, e.g., U.S. Pat. Nos: 6,190,923, 6,187,285, 6,183,721, 6,177,562, 6,159,445, 6,153,775, 6,149,890, 6,143,276, 6,143,274, 6,139,819, 6,132,764, 6,123,923, 6,123,921, 6,120,768, 6,120,751, 6,117,412, 6,106,866, 6,096,290, 6,093,382, 6,090,800, 6,090,408, 6,088,613, 6,077,499, 6,075,010, 6,071,494, 6,071,490, 6,060,040, 6,056,939, 6,051,207, 6,048,979, 6,045,821, 6,045,775, 6,030,840, 6,028,066, 6,022,966, 6,022,523, 6,022,522, 6,017,522, 6,015,897, 6,010,682, 6,010,681, 6,004,533, and 6,001,329).

3) Production of Fusion Proteins

Where the MUC-1 targeting molecule and/or the effector molecule is relatively short (i.e., less than about 50 amino acids) they may be synthesized using standard chemical peptide synthesis techniques. Where both molecules are relatively short the chimeric molecule may be synthesized as a single contiguous polypeptide. Alternatively the targeting molecule and the effector molecule may be synthesized separately and then fused by condensation of the amino terminus of one molecule with the carboxyl terminus of the other molecule thereby forming a peptide bond. Alternatively, the targeting and effector molecules may each be condensed with one end of a peptide spacer molecule thereby forming a contiguous fusion protein.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis*; pp. 3–284 in *The Peptides: Analysis, Synthesis, Biology. Vol. 2: Special Methods in Peptide Synthesis*, Part A., Merrifield, et al. *J. Am. Chem. Soc.*, 85: 2149–2156 (1963), and Stewart et al., *Solid Phase Peptide Synthesis*, 2nd ed. Pierce Chem. Co., Rockford, Ill. (1984).

In a preferred embodiment, the chimeric fusion proteins of the present invention are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins (e.g. anti-MUC-1-PE38QQR) of this invention may be prepared by any suitable method, including, for example, cloning and restriction of appropriate sequences or direct chemical synthesis by methods such as the phosphotriester method of Narang et al. (1979) *Meth. Enzymol.* 68: 90–99; the phosphodiester method of Brown et al. (1979) *Meth. Enzymol.* 68: 109–151; the diethylphosphoramidite method of Beaucage et al. (1981) *Tetra. Lett.*, 22: 1859–1862; and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences can be obtained by the ligation of shorter sequences.

Alternatively, subsequences can be cloned and the appropriate subsequences cleaved using appropriate restriction enzymes. The fragments can then be ligated to produce the desired DNA sequence.

In a preferred embodiment, DNA encoding fusion proteins of the present invention may be cloned using DNA amplification methods such as polymerase chain reaction (PCR). Thus, for example, the nucleic acid encoding an anti-MUC-1 antibody is PCR amplified, using a sense primer containing the restriction site for NdeI and an antisense primer containing the restriction site for HindIII. This produces a nucleic acid encoding the anti-MUC-1 sequence and having terminal restriction sites. A PE38QQR fragment may be cut out of the plasmid pWDMH4–38QQR or plasmid pSGC242FdN1 described by Debinski et al. (1994) *Int. J. Cancer*, 58: 744–748. Ligation of the anti-MUC-1 and PE38QQR sequences and insertion into a vector produces a vector encoding anti-MUC-1 joined to the amino terminus of PE38QQR (position 253 of PE). The two molecules are joined by a three amino acid junction consisting of glutamic acid, alanine, and phenylalanine introduced by the restriction site.

While the two molecules are preferably essentially directly joined together, one of skill will appreciate that the molecules may be separated by a peptide spacer consisting of one or more amino acids. Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

The nucleic acid sequences encoding the fusion proteins may be expressed in a variety of host cells, including *E. coli*, other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes (1982) *Protein Purification*, Springer-Verlag, N.Y.; Deutscher (1990) *Methods in Enzymology Vol. 182: Guide to Protein Purification.*, Academic Press, Inc. N.Y.). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the MUC-1 targeted fusion protein may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (See, Debinski et al. (1993) *J. Biol. Chem.*, 268: 14065–14070; Kreitman and Pastan (1993) *Bioconjug. Chem.*, 4: 581–585; and Buchner, et al. (1992) *Anal. Biochem.*, 205: 263–270).

One of skill would recognize that modifications can be made to the MUC-1 targeted fusion proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

III. Preparation and Modification of Anti-MUC-1 Antibodies.

As described below, using the information provided herein, anti-MUC-1 antibodies of this invention can be prepared using either chemical synthetic means or by the use of recombinant expression systems. In addition, other "related" anti-MUC-1 antibodies can be identified by screening for antibodies that bind to the same epitope and/or by modification of the anti-MUC-1 antibodies (e.g., 12E, 3D, A5, C4, B5, E1, and B9) to produce libraries of modified antibody and then rescreening antibodies in the library for improved MUC-1 avidity.

A) Antibody Synthesis.

1) Chemical Synthesis.

Using the sequence information provided herein, the anti-MUC-1 antibodies of this invention (e.g., 12E, 3D, A5, C4, B5, E1, and B9), or variants thereof, can be chemically synthesized using well known methods of peptide synthesis. Solid phase synthesis in which the C-terminal amino acid of the sequence is attached to an insoluble support followed by sequential addition of the remaining amino acids in the sequence is one preferred method for the chemical synthesis of single chain antibodies. Techniques for solid phase synthesis are described by Barany and Merrifield, *Solid Phase Peptide Synthesis*; pp. 3–284 in *The Peptides: Analysis, Synthesis, Biology*. Vol. 2: *Special Methods in Peptide Synthesis*, Part A., Merrifield et al. (1963) *J. Am. Chem. Soc.*, 85: 2149–2156, and Stewart et al. (1984) *Solid Phase Peptide Synthesis*, 2nd ed. Pierce Chem. Co., Rockford, Ill..

2) Recombinant expression of anti-MUC-1 antibodies

In certain preferred embodiments, the anti-MUC-1 antibodies of this invention (e.g., 12E, 3D, A5, C4, B5, E1, and B9), or variants thereof, are prepared using standard techniques well known to those of skill in the art. Using the sequence information provided herein, nucleic acids encoding the desired antibody can be chemically synthesized according to a number of standard methods known to those of skill in the art. Oligonucleotide synthesis, is preferably carried out on commercially available solid phase oligonucleotide synthesis machines (Needham-VanDevanter et al. (1984) *Nucleic Acids Res.* 12: 6159–6168) or manually synthesized using the solid phase phosphoramidite triester method described by Beaucage et. al. (Beaucage et. al. (1981) *Tetrahedron Letts*. 22(20): 1859–1862). Alternatively, nucleic acids encoding the antibody can be amplified and/or cloned according to standard methods.

Molecular cloning techniques to achieve these ends are known in the art. A wide variety of cloning and in vitro amplification methods are suitable for the construction of recombinant nucleic acids. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning A Laboratory Manual* (2nd ed.) Vol. 1–3, Cold Spring Harbor Laboratory, Cold Spring Harbor Press, N.Y., (Sambrook); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Methods of producing recombinant immunoglobulins are also known in the art. See, Cabilly, U.S. Pat. No. 4,816,567; and Queen et al. (1989) *Proc. Natl Acad. Sci. USA* 86: 10029–10033. In addition, detailed protocols for the expression of the antibodies of this invention are provided herein in the Examples.

B) Identification of other Antibodies Binding the Same Epitope as 12E, 3D, A5, C4, B5, E1, and/or B9.

Having identified useful anti-MUC-1 antibodies (e.g., 12E, 3D, A5, C4, B5, E1, and B9), other "related" anti-MUC-1 antibodies can be identified by screening for antibodies that cross-react with the identified antibodies, either at the epitope bound by the antibodies or with an idiotypic antibody raised against the anti-MUC-1 antibodies of this invention.

1) Cross-reactivity with Anti-idiotypic Antibodies

The idiotype represents the highly variable antigen-binding site of an antibody and is itself immunogenic. During the generation of an antibody-mediated immune response, an individual will develop antibodies to the antigen as well as anti-idiotype antibodies, whose immunogenic binding site (idiotype) mimics the antigen.

Anti-idiotypic antibodies can be raised against the variable regions of the antibodies identified herein using standard methods well known to those of skill in the art. Briefly, anti-idiotype antibodies can be made by injecting the antibodies of this invention, or fragments thereof (e.g., CDRs) into an animal thereby eliciting antisera against various antigenic determinants on the antibody, including determinants in the idiotypic region.

Methods for the production of anti-analyte antibodies are well known in the art. Large molecular weight antigens (greater than approx. 5000 Daltons) can be injected directly into animals, whereas small molecular weight compounds (less than approx. 5000 Daltons) are preferably coupled to a high molecular weight immunogenic carrier, usually a protein, to render them immunogenic. The antibodies produced in response to immunization can be utilized as serum, ascites fluid, an immunoglobulin (Ig) fraction, an IgG fraction, or as affinity-purified monospecific material.

Polyclonal anti-idiotype antibodies can be prepared by immunizing an animal with the antibodies of this invention prepared as described above. In general, it is desirable to immunize an animal which is species and allotype-matched with the animal from which the antibody (e.g. phage-display library) was derived. This minimizes the production of antibodies directed against non-idiotypic determinants. The antiserum so obtained is then usually absorbed extensively against normal serum from the same species from which the phage-display library was derived, thereby eliminating antibodies directed against non-idiotypic determinants. Absorption can be accomplished by passing antiserum over a gel formed by crosslinking normal (nonimmune) serum proteins with glutaraldehyde. Antibodies with anti-idiotypic specificity will pass directly through the gel, while those having specificity for non-idiotypic determinants will bind to the gel. Immobilizing nonimmune serum proteins on an insoluble polysaccharide support (e.g., sepharose) also provides a suitable matrix for absorption.

Monoclonal anti-idiotype antibodies can be produced using the method of Kohler et al. (1975) *Nature* 256: 495. In particular, monoclonal anti-idiotype antibodies can be prepared using hybridoma technology which comprises fusing (1) spleen cells from a mouse immunized with the antigen or hapten-carrier conjugate of interest (i.e., the antibodies or this invention or subsequences thereof) to (2) a mouse myeloma cell line which has been selected for resistance to a drug (e.g., 8-azaguanine). In general, it is desirable to use a myeloma cell line which does not secrete an immunoglobulin. Several such lines are known in the art. A preferred cell line is P3X63Ag8.653. This cell line is on deposit at the American Type Culture Collection as CRL-1580.

Fusion can be carried out in the presence of polyethylene glycol according to established methods (see, e.g., *Monoclonal Antibodies*, R. Kennett, J. McKearn & K. Bechtol, eds. N.Y., Plenum Press, 1980, and *Current Topics in Microbiology & Immunology*, Vol. 81, F. Melchers, M. Potter & N. L. Warner, eds., N.Y., Springer-Verlag, 1978). The resultant mixture of fused and unfused cells is plated out in hypoxanthine-aminopterin-thymidine (HAT) selective medium. Under these conditions, only hybrid cells will grow.

When sufficient cell growth has occurred, (typically 10–14 days post-fusion), the culture medium is harvested and screened for the presence of monoclonal idiotypic, anti-analyte antibody by any one of a number of methods which include solid phase RIA and enzyme-linked immunosorbent assay. Cells from culture wells containing antibody of the desired specificity are then expanded and recloned. Cells from those cultures that remain positive for the antibody of interest are then usually passed as ascites tumors in susceptible, histocompatible, pristane-primed mice.

Ascites fluid is harvested by tapping the peritoneal cavity, retested for antibody, and purified as described above. If a nonsecreting myeloma line is used in the fusion, affinity purification of the monoclonal antibody is not usually necessary since the antibody is already homogeneous with respect to its antigen-binding characteristics. All that is necessary is to isolate it from contaminating proteins in ascites, i.e., to produce an immunoglobulin fraction.

Alternatively, the hybrid cell lines of interest can be grown in serum-free tissue culture and the antibody harvested from the culture medium. In general, this is a less desirable method of obtaining large quantities of antibody because the yield is low. It is also possible to pass the cells intravenously in mice and to harvest the antibody from serum. This method is generally not preferred because of the small quantity of serum which can be obtained per bleed and because of the need for extensive purification from other serum components. However, some hybridomas will not grow as ascites tumors and therefore one of these alternative methods of obtaining antibody must be used.

2) Cross-reactivity with the Anti-MUC-1 Antibodies of this Invention.

Instead of the anti-idiotypic antibody, other anti-MUC-1 antibodies of this invention can be identified by the fact that they bind the same epitope as the "prototypic" antibodies of this invention (e.g., 12E, 3D, A5, C4, B5, E1, B9, etc.). Methods of determining antibody cross-reactivity are well known to those of skill in the art. Generally the epitope bound by the prototypic antibodies of this invention is determined e.g. by epitope mapping techniques. Methods of epitope mapping are well known to those of skill in the art (see, e.g., Reyes et al. (1992) *Hepatitis E Virus* (HEV): *Epitope Mapping and Detection of Strain Variation*, Elsevier Science Publisher Shikata et al. eds., Chapter 43:237–245; Li et al. (1993) *Nature* 363: 85–88). Epitope mapping can be performed usign Novatope system, a kit for which is commercially available from Novagen, Inc.

Once the epitope bound by the prototypic antibodies of this invention is elucidated, the ability of newly generated anti-MUC-1 antibodies to bind the same epitope is determined, e.g. using standard immune assays such as a sandwich assay, a biaCore assay, etc. Examples of a cross-reactivity assay are provided in U.S. Pat. No. 6,197,938. Preferred cross-reactive anti-MUC-1 antibodies show at least 60%, preferably 80%, more preferably 90%, and most preferably at least 95% or at least 99% cross-reactivity with one or more of the prototypic antibodies of this invention..

C) Phase Display Methods to Select other "Related" Anti-MUC-1 Antibodies.

1) Chain Shuffling Methods.

To create higher affinity antibodies, mutant scFv gene repertories, based on the sequence of a binding of an identified anti-MUC-1 antibody (e.g., 12E, 3D, A5, C4, B5, E1, B9, etc.), are created and expressed on the surface of phage. Higher affinity scFvs are selected on antigen, e.g. as described above.

One approach to creating modified single-chain antibody (scFv) gene repertoires has been to replace the original $V_H$ or $V_L$ gene with a repertoire of V-genes to create new partners (chain shuffling) (Clackson et al. (1991) *Nature*. 352: 624–628). Using chain shuffling and phage display, the affinity of a human scFv antibody fragment that bound the hapten phenyloxazolone (phOx) was increased from 300 nM to 1 nM (300 fold) (Marks et al. (1992) *Bio/Technology* 10: 779–783).

Thus, for example, to alter the affinity of an anti-MUC-1 antibody, a mutant scFv gene repertoire can be created containing the $V_H$ gene of the anti-MUC-1 antibodies (e.g., 12E, 3D, A5, C4, B5, E1, B9, etc.) antibody and a human $V_L$ gene repertoire (light chain shuffling). The scFv gene repertoire can be cloned into a phage display vector, e.g., pHEN-1 (Hoogenboom et al. (1991) *Nucleic Acids Res.*, 19: 4133–4137) and after transformation a library of transformants is obtained.

Similarly, for heavy chain shuffling, the anti-MUC-1 antibody (e.g., 12E, 3D, A5, C4, B5, E1, B9, etc.) antibody $V_H$ CDR1 and/or CDR2, and/or CDR3 and light chain are cloned into a vector containing a human $V_H$ gene repertoire to create a phage antibody library transformants. For detailed descriptions of chain shuffling to increase antibody affinity see Schier et al. (1996) *J. Mol. Biol.*, 255: 28–43, 1996.

2) Site-directed Mutagenesis to Improve Binding Affinity

The majority of antigen contacting amino acid side chains are typically located in the complementarity determining regions (CDRs), three in the $V_H$ (CDR1, CDR2, and CDR3) and three in the $V_L$ (CDR1, CDR2, and CDR3) (Chothia et al. (1987) *J. Mol. Biol.*, 196: 901–917; Chothia et al. (1986) *Science*, 233: 755–8; Nhan et al. (1991) *J. Mol. Biol.*, 217: 133–151). These residues contribute the majority of binding energetics responsible for antibody affinity for antigen. In other molecules, mutating amino acids which contact ligand has been shown to be an effective means of increasing the affinity of one protein molecule for its binding partner (Lowman et al. (1993) *J. Mol. Biol.*, 234: 564–578; Wells (1990) *Biochemistry*, 29: 8509–8516). Site-directed mutagenesis of CDRs and screening against MUC-1 antibodies having improved binding affinity.

3) CDR Randomization to Produce Higher Affinity Human scFv

In an extension of simple site-directed mutagenesis, mutant antibody libraries can be created where partial or entire CDRs are randomized ($V_L$ CDR1 and CDR2 and $V_H$ CDR1, CDR2 and CDR3). In one embodiment, each CDR is randomized in a separate library, using the known anti-MUC-1 antibody (e.g., 12E, 3D, A5, C4, B5, E1, B9, etc.) as a template. The CDR sequences of the highest affinity mutants from each CDR library are combined to obtain an additive increase in affinity. A similar approach has been used to increase the affinity of human growth hormone (hGH) for the growth hormone receptor over 1500 fold from $3.4 \times 10^{-10}$ to $9.0 \times 10^{-13}$ M (Lowman et al. (1993) *J. Mol. Biol.*, 234: 564–578).

$V_H$ CDR3 often occupies the center of the binding pocket, and thus mutations in this region are likely to result in an increase in affinity (Clackson et al. (1995) *Science*, 267: 383–386). In one embodiment, four $V_H$ CDR3 residues are randomized at a time using the nucleotides NNS (see, e.g., Schier et al. (1996) *Gene*, 169: 147–155; Schier and Marks (1996) *Human Antibodies and Hybridomas*. 7: 97–105, 1996; and Schier et al. (1996) *J. Mol. Biol.* 263: 551–567, 1996).

4) Creation of Homodimers

To create (scFv')$_2$ antibodies, two anti-MUC-1 scFvs are joined, either through a linker (e.g., a carbon linker, a peptide, etc.) or through a disulfide bond between, for example, two cysteins. Thus, for example, to create disulfide linked scFv, a cysteine residue is introduced by site directed mutagenesis at the carboxy-terminus of the antibodies described herein.

An scFv can be expressed from this construct, purified by IMAC, and analyzed by gel filtration. To produce (scFv')$_2$ dimers, the cysteine is reduced by incubation with 1 mM Ǝ-mercaptoethanol, and half of the scFv blocked by the addition of DTNB. Blocked and unblocked scFvs are incubated together to form (scFv')$_2$ and the resulting material can be analyzed by gel filtration. The affinity of the resulting dimmer can be determined using standard methods, e.g. by BIAcore.

In a particularly preferred embodiment, the (scFv')$_2$ dimer is created by joining the scFv' fragments through a linker, more preferably through a peptide,linker. This can be accomplished by a wide variety of means well known to those of skill in the art. For example, one preferred approach is described by Holliger et al. (1993) *Proc. Natl. Acad. Sci. USA*, 90: 6444–6448 (see also WO 94/13804).

5) Measurement of Antibody/Polypeptide Binding Affinity

As explained above, selection for increased avidity involves measuring the affinity of the antibody for the target antigen (e.g., MUC-1). Methods of making such measurements are well known to, those of skill in the art. Briefly, for example, the $K_d$ of 3D-, A5-, C4-, 12E, B5-, E1-, or B9-derived antibody are determined from the kinetics of binding to MUC-1 in a BIAcore, a biosensor based on surface plasmon resonance. For this technique, antigen is coupled to a derivatized sensor chip capable of detecting changes in mass. When antibody is passed over the sensor chip, antibody binds to the antigen resulting in an increase in mass that is quantifiable. Measurement of the rate of association as a function of antibody concentration can be used to calculate the association rate constant ($k_{on}$). After the association phase, buffer is passed over the chip and the rate of dissociation of antibody ($k_{off}$) determined. $K_{on}$ is typically measured in the range $1.0 \times 10^2$ to $5.0 \times 10^6$ and $k_{off}$ in the range $1.0 \times 10^{-1}$ to $1.0 \times 10^{-6}$. The equilibrium constant $K_d$ is often calculated as $k_{off}/k_{on}$ and thus is typically measured in the range $10^{-5}$ to $10^{-12}$. Affinities measured in this manner correlate well with affinities measured in solution by fluorescence quench titration.

D) Human Antibodies, Humanized Antibodies, Chimeric Antibodies and Diabodies.

The antibodies described herein and/or the VH and/or VL domains therein can be used to make a variety of human, or humanized antibodies or diabodies.

i) Humanized (Chimeric) Antibodies

The antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; Morrison et al. (1984) *Proc. Natl. Acad. Sci.* 81: 6851–6855, etc.).

Humanized (chimeric) antibodies are immunoglobulin molecules comprising a human and non-human portion. More specifically, the antigen combining region (or variable region) of a humanized chimeric antibody is derived from a non-human source (e.g., murine) and the constant region of the chimeric antibody (which confers biological effector function to the immunoglobulin) is derived from a human source. The humanized chimeric antibody will have the antigen binding specificity of the non-human antibody molecule and the effector function conferred by the human antibody molecule. A large number of methods of generating chimeric antibodies are well known to those of skill in the art (see, e.g., U.S. Pat. Nos: 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369, and PCT application WO 91/0996).

In general, the procedures used to produce chimeric antibodies consist of the following steps (the order of some steps may be interchanged): (a) identifying and cloning the correct gene segment encoding the antigen binding portion of the antibody molecule; this gene segment (known as the VDJ, variable, diversity and joining regions for heavy chains or VJ, variable, joining regions for light chains, or simply as the V or variable region or $V_H$ and $V_L$ regions) may be in either the cDNA or genomic form; (b) cloning the gene segments encoding the human constant region or desired part thereof; (c) ligating the variable region to the constant region so that the complete chimeric antibody is encoded in a transcribable and translatable form; (d) ligating this construct into a vector containing a selectable marker and gene control regions such as promoters, enhancers and poly(A) addition signals; (e) amplifying this construct in a host cell (e.g., bacteria); (f) introducing the DNA into eukaryotic cells (transfection) most often mammalian lymphocytes; and culturing the host cell under conditions suitable for expression of the chimeric antibody.

Antibodies of several distinct antigen binding specificities have been manipulated by these protocols to produce chimeric proteins (e.g., anti-TNP: Boulianne et al. (1984) Nature, 312: 643; and anti-tumor antigens: Sahagan et al. (1986) J. Immunol., 137: 1066). Likewise several different effector functions have been achieved by linking new sequences to those encoding the antigen binding region. Some of these include enzymes (Neuberger et al. (1984) Nature 312: 604), immunoglobulin constant regions from another species and constant regions of another immunoglobulin chain (Sharon et al. (1984) Nature 309: 364; Tan et al., (1985) J. Immunol. 135: 3565–3567).

In one preferred embodiment, a recombinant DNA vector is used to transfect a cell line that produces an anti-MUC-1 antibody of this invention. The novel recombinant DNA vector contains a "replacement gene" to replace all or a portion of the gene encoding the immunoglobulin constant region in the cell line (e.g., a replacement gene may encode all or a portion of a constant region of a human immunoglobulin, a specific immunoglobulin class, or an enzyme, a toxin, a biologically active peptide, a growth factor, inhibitor, or a linker peptide to facilitate conjugation to a drug, toxin, or other molecule, etc.), and a "target sequence" that allows for targeted homologous recombination with immunoglobulin sequences within the antibody producing cell.

In another embodiment, a recombinant DNA vector is used to transfect a cell line that produces an antibody having a desired effector function, (e.g., a constant region of a human immunoglobulin) in which case, the replacement gene contained in the recombinant vector may encode all or a portion of a region of an anti MUC-1 antibody of this invention and the target sequence contained in the recombinant vector allows for homologous recombination and targeted gene modification within the antibody producing cell. In either embodiment, when only a portion of the variable or constant region is replaced, the resulting chimeric antibody can define the same antigen and/or have the same effector function yet be altered or improved so that the chimeric antibody may demonstrate a greater antigen specificity, greater affinity binding constant, increased effector function, or increased secretion and production by the transfected antibody producing cell line, etc.

Regardless of the embodiment practiced, the processes of selection for integrated DNA (via a selectable marker), screening for chimeric antibody production, and cell cloning, can be used to obtain a clone of cells producing the chimeric antibody.

Thus, a piece of DNA that encodes a modification for a monoclonal antibody can be targeted directly to the site of the expressed immunoglobulin gene within a B-cell or hybridoma cell line. DNA constructs for any particular modification may be can to alter the protein product of any monoclonal cell line or hybridoma. The level of expression of chimeric antibody should be higher when the gene is at its natural chromosomal location rather than at a random position. Detailed methods for preparation of chimeric (humanized) antibodies can be found in U.S. Pat. No. 5,482,856.

ii) Human Antibodies

In another embodiment, this invention provides for fully human anti-MUC-1 antibodies. Human antibodies consist entirely of characteristically human polypeptide sequences. The human anti-MUC-1-neutralizing antibodies of this invention can be produced in using a wide variety of methods (see, e.g., Larrick et al., U.S. Pat. No. 5,001,065, for review).

In one embodiment, fully human antibodies are produced using phage display methods. However, instead of utilizing a murine gene library, a human gene library is used. Methods of producing fully human gene libraries are well known to those of skill in the art (see, e.g., Vaughn et al. (1996) Nature Biotechnology, 14(3): 309–314, Marks et al. (1991) J. Mol. Biol., 222: 581–597, and PCT/US96/10287).

The human phage-display library is screened for members that bind the same epitope (e.g. are cross-reactive) with the anti-MUC-1 antibodies described herein.

In another approach, the human antibodies are produced using trioma technology. The general approach for producing human antibodies by trioma technology has been described by Ostberg et al. (1983) Hybridoma 2: 361–367, Ostberg, U.S. Pat. No. 4,634,664, and Engelman et al., U.S. Pat. No. 4,634,666. The antibody-producing cell lines obtained by this method are called triomas because they are descended from three cells; two human and one mouse. Triomas have been found to produce antibody more stably than ordinary hybridomas made from human cells.

Preparation of trioma cells requires an initial fusion of a mouse myeloma cell line with unimmunized human peripheral B lymphocytes. This fusion generates a xenogenic hybrid cell containing both human and mouse chromosomes (see, Engelman, supra.). Xenogenic cells that have lost the capacity to secrete antibodies are selected. Preferably, a xenogenic cell is selected that is resistant to 8-azaguanine. Such cells are unable to propagate on hypoxanthine-aminopterin-thymidine (HAT) or azaserine-hypoxanthine (AH) media.

The capacity to secrete antibodies is conferred by a further fusion between the xenogenic cell and B-lymphocytes immunized against a MUC-1 antigen. The B-lymphocytes are obtained from the spleen, blood or lymph nodes of human donor. If antibodies against a specific antigen or epitope are desired (e.g. the epitope(s) bound by the antibodies described herein), it is preferable to use that antigen or epitope thereof as the immunogen. Alternatively, B-lymphocytes are obtained from an unimmunized individual and stimulated with the desired antigen in vitro.

The immunized B-lymphocytes prepared by one of the above procedures are fused with a xenogenic hybrid cell by well known methods. For example, the cells are treated with 40–50% polyethylene glycol of MW 1000–4000, at about 37° C. for about 5–10 min. Cells are separated from the fusion mixture and propagated in media selective for the desired hybrids. When the xenogenic hybrid cell is resistant to 8-azaguanine, immortalized trioma cells are conveniently selected by successive passage of cells on HAT or AH medium. Other selective procedures are, of course, possible depending on the nature of the cells used in fusion. Clones secreting antibodies having the required binding specificity are identified by assaying the trioma culture medium for the ability to bind to the epitope(s) bound by the antibodies exemplified herein. Triomas producing human antibodies having the desired specificity are subcloned by the limiting dilution technique and grown in vitro in culture medium, or are injected into selected host animals and grown in vivo.

Although triomas are genetically stable they do not produce antibodies at very high levels. Expression levels can be increased by cloning antibody genes from the trioma into one or more expression vectors, and transforming the vector into a cell line such as the cell lines typically used for expression of recombinant or humanized immunoglobulins. As well as increasing yield of antibody, this strategy offers the additional advantage that immunoglobulins are obtained from a cell line that does not have a human component, and does not therefore need to be subjected to the especially extensive viral screening required for human cell lines.

The genes encoding the heavy and light chains of immunoglobulins secreted by trioma cell lines are cloned according to methods, including but not limited to, the polymerase chain reaction (PCR), known in the art (see, e.g., Sambrook et al., *Molecular Cloning: A Laboratory Manual*, 2nd ed., Cold Spring Harbor, N.Y., 1989; Berger & Kimmel, *Methods in Enzymology, Vol.* 152: *Guide to Molecular Cloning Techniques*, Academic Press, Inc., San Diego, Calif., 1987; Co et al. (1992) *J. Immunol.*, 148: 1149). For example, genes encoding heavy and light chains are cloned from a trioma's genomic DNA or cDNA produced by reverse transcription of the trioma's RNA. Cloning is accomplished by conventional techniques including the use of PCR primers that hybridize to the sequences flanking or overlapping the genes, or segments of genes, to be cloned.

Typically, recombinant constructs comprise DNA segments encoding a complete human immunoglobulin heavy chain and/or a complete human immunoglobulin light chain of an immunoglobulin expressed by a trioma cell line. Alternatively, DNA segments encoding only a portion of the primary antibody genes are produced, which portions possess binding and/or effector activities. Other recombinant constructs contain segments of trioma cell line immunoglobulin genes fused to segments of other immunoglobulin genes, particularly segments of other human constant region sequences (heavy and/or light chain). Human constant region sequences can be selected from various reference sources, including but not limited to those listed in Kabat et al. (1987) *Sequences of Proteins of Immunological Interest*, U.S. Department of Health and Human Services.

iii) Diabodies

In certain embodiments, this invention contemplates diabodies comprising one or more of the $V_H$ and $V_L$ domains described herein. The term "diabodies" refers to antibody fragments typically having two antigen-binding sites. The fragments typically comprise a heavy chain variable domain ($V_H$) connected to a light chain variable domain ($V_L$) in the same polypeptide chain ($V_H$–$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Holliger et al. (1993) *Proc. Natl. Acad. Sci. USA* 90: 6444–6448.

III. Libraries and Vectors.

In another embodiment, this invention provides libraries and vectors for practice of the methods described herein. The libraries include monovalent or polyvalent libraries, including diabody libraries and more preferably including multi-valent single chain antibody libraries (e.g. scFv), (e.g., expressed by phage).

The libraries can take a number of forms. Thus, in one embodiment the library is a collection of cells containing members of the phage display library, while in another embodiment, the library consists of a collection of isolated phage, and in still another embodiment, the library consists of a library of nucleic acids encoding a polyvalent phage display library. In certain embodiment, the nucleic acids can be phagemid vectors encoding the antibodies and ready for subcloning into a phage vector or the nucleic acids can be a collection of phagemid already carrying the subcloned antibody-encoding nucleic acids.

IV) Pharmaceutical Compositions.

The anti-MUC-1 antibodies, and/or chelates, and/or chimeric molecules of this invention are useful for parenteral, topical, oral, or local administration (e.g. injected into a tumor site), aerosol administration, or transdermal administration, for prophylactic, but principally for therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the fusion proteins and pharmaceutical compositions of this invention, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting proteins from digestion are well known in the art.

The pharmaceutical compositions of this invention are particularly useful for parenteral administration, such as intravenous administration or administration into a body cavity or lumen of an organ. The compositions for administration will commonly comprise a solution of the chimeric molecule dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of chimeric molecule in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Actual methods for preparing parenterally administrable compositions will be known or apparent to those skilled in the art and are described in more detail in such publications as *Remington's Pharmaceutical Science*, 15th ed., Mack Publishing Company, Easton, Pa. (1980).

The compositions containing the present fusion proteins or a cocktail thereof (i.e., with other proteins) can be administered for therapeutic treatments. In therapeutic applications, compositions are administered to a patient suffering from a disease, e.g., a cancer, in an amount sufficient to cure or at least partially arrest the disease and its complications. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the proteins of this invention to effectively treat the patient.

It will be appreciated by one of skill in the art that there are some regions that are not heavily vascularized or that are protected by cells joined by tight junctions and/or active transport mechanisms which reduce or prevent the entry of macromolecules present in the blood stream. Thus, for example, systemic administration of therapeutics to treat gliomas, or other brain cancers, is constrained by the blood-brain barrier which resists the entry of macromolecules into the subarachnoid space.

One of skill in the art will appreciate that in these instances, the therapeutic compositions of this invention can be administered directly to the tumor site. Thus, for example, brain tumors (e.g., gliomas) can be treated by administering the therapeutic composition directly to the tumor site (e.g., through a surgically implanted catheter). Where the fluid delivery through the catheter is pressurized, small molecules (e.g. the therapeutic molecules of this invention) will typically infiltrate as much as two to three centimeters beyond the tumor margin.

Alternatively, the therapeutic composition can be placed at the target site in a slow release formulation. Such formulations can include, for example, a biocompatible sponge or other inert or resorbable matrix material impregnated with the therapeutic composition, slow dissolving time release capsules or microcapsules, and the like.

Typically the catheter or time release formulation will be placed at the tumor site as part of a surgical procedure. Thus, for example, where major tumor mass is surgically removed, the perfusing catheter or time release formulation can be emplaced at the tumor site as an adjunct therapy. Of course, surgical removal of the tumor mass may be undesired, not required, or impossible, in which case, the delivery of the therapeutic compositions of this invention may comprise the primary therapeutic modality.

VIII. Kits.

Where a radioactive, or other, effector is used as a diagnostic and/or therapeutic agent, it is a frequently impossible to put the ready-for-use composition at the disposal of the user, because of the often poor shelf life of the radiolabelled compound and/or the short half-life of the radionuclide used. In such cases the user can carry out the labeling reaction with the radionuclide in the clinical hospital, physician's office, or laboratory. For this purpose, or other purposes, the various reaction ingredients can then be offered to the user in the form of a so-called "kit". The kit is preferably designed so that the manipulations necessary to perform the desired reaction should be as simple as possible to enable the user to prepare from the kit the desired composition by using the facilities that are at his disposal. Therefore the invention also relates to a kit for preparing a composition according to this invention..

Such a kit according to the present invention preferably comprises an anti-MUC-1 antibody of this invention. The antibody can be provided, if desired, with inert pharmaceutically acceptable carrier and/or formulating agents and/or adjuvants is/are added. In addition, the kit optionally includes a solution of a salt or chelate of a suitable radionuclide (or other active agent), and (iii) instructions for use with a prescription for administering and/or reacting the ingredients present in the kit.

The kit to be supplied to the user may also comprise the ingredient(s) defined above, together with instructions for use, whereas the solution of a salt or chelate of the radionuclide, defined sub (ii) above, which solution has a limited shelf life, may be put to the disposal of the user separately.

The kit can optionally, additionally comprise a reducing agent and/or, if desired, a chelator, and/or instructions for use of the composition and/or a prescription for reacting the ingredients of the kit to form the desired product(s). If desired, the ingredients of the kit may be combined, provided they are compatible.

In certain embodiments, the complex-forming reaction with the anti-MUC-1 antibody can simply be produced by combining the components in a neutral medium and causing them to react. For that purpose the effector may be presented to the anti-MUC-1 antibody in the form of a chelate.

When kit constituent(s) are used as component(s) for pharmaceutical administration (e.g. as an injection liquid) they should be sterile. When the constituent(s) are provided in a dry state, the user should preferably use a sterile physiological saline solution as a solvent. If desired, the constituent(s) may be stabilized in the conventional manner with suitable stabilizers, for example, ascorbic acid, gentisic acid or salts of these acids, or they may comprise other auxiliary agents, for example, fillers, such as glucose, lactose, mannitol, and the like.

While the instructional materials, when present, typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Preclinical Development of Anti-MUC-1 scFv for Targeted Therapy

The MUC-1 mucin is a large complex glycoprotein that is overexpressed and under or aberrantly glycosylated on many malignant epithelial cancers making it an attractive antigen for cancer diagnostics and therapy agents. Radiolabled monoclonal antibodies against the MIUC-1 mucin used to deliver targeted radiation to metastatic breast adenocarcinoma have been met with only modest success due to the large size of the antibody molecule (150 kD) which protracts delivery of cytotoxic radiation to the tumor(s)and prolongs the radioactivity in the circulation or normal organs. These experiments identified several anti-MUC-1 single chain fragment antibodies (randomly linked $V_H$ and $V_L$ antigen biding region of immunoglobulin molecules) which had characteristics suitable to use as modules of molecules used to deliver targeted radiation more effectively to tumors. Seven anti-MUC-1 single-chain Fv antibody fragments (scFv) were selected from a phage display library by binding synthetic peptide core tandem repeat and by ELISA analysis, demonstrating the highest specific binding to the MUC-1 positive MCF-7 breast adenocarcinoma cells. Sequence analysis revealed that five of the seven scFv had an expected scFv sequence ($V_H$-Gly$_4$(Ser)$_3$ linker (SEQ ID NO:22)-$V_L$) while one of the scFv contained only the $V_H$ antigen binding region and another contained only the $V_L$ antigen binding region. Competitive ELISA analysis demonstrated that four of the scFv were inhibited by at least 50% with 1 nM of competitor; A5 (89%), C4 (94%), 3D (50%) and 12E (50%). Regression analysis of competitive ELISA demonstrated affinities ($K_a$) of all scFv to be greater than $1.5 \times 10^8$; C4 ($K_a=8.2 \times 10^8$), A5 ($K_a=7.1 \times 10^8$), 3D ($K_a=2.2 \times 10^8$) and 12E ($K_a=1.7 \times 10^8$). Scatchard analysis of $^{125}$I-labeled bivalent and monovalent forms of the 12E scFv demonstrated the bivalent form of the 12E scFv had the identical Ka that was derived from regression analysis while the monomeric form of the 12E scFv had a Ka=$8.6 \pm 1.1 \times 10^7$ M$^7$. Immunopathologic analysis demonstrated 12E scFv to be strongly reactive with the MCF-7 cells. Molecular modeling showed good homology of the 12E scFv with the crystal structure of the MFE-23 scFv. These anti-MUC-1 scFv are being used as antigen binding modules in new agents for detection and therapy of cancer.

Materials and Methods.

MUC-1 antigen positive human breast adenocarcinoma cell line MCF-7 cells (American Type Culture Collection (ATCC), Manassas, Va.) were grown to 75% confluence in DMEM media containing 5% FBS and harvested. MCF-7 lysate containing membrane fragments were obtained for ELISA analysis based upon a previously described protocol (Gorga et al. (1987) *J. Biol. Chem.*, 252: 16087–16094). Total protein amount of the MCF-7 cell membrane lysate was determined using the Micro BCA protein assay reagent kit (Pierce Chemical Co., Rockford, Ill.). Raji cells (ATCC) were grown in RPMI 1640 media containing 10% FBS.

Anti-MUC-1 Library Construction.

Briefly, Balb/c mice (Harlan Sprague Dawley, Indianapolis, Ind.) received an intraperitoneal injection of MUC-1 positive MCF-7/HBT 3477 (10:1) cell membrane lysate, followed by three immunizations of KLH-MUC-1 synthetic peptide at three weak intervals (Id.). Serum IgG levels collected 10 days post-immunization were tested by ELISA against MCF-7 cell membrane lysate. The RNA obtained from the spleens of the immunized mice were removed and mRNA purified using the mRNA purification kit (Amersham Pharmacia Biotech); cDNA synthesis, $V_H$ and $V_L$ gene amplification, scFv assembly, and ligation into the pCANTAB 5E vector were carried out using the RPAS mouse scFv module (Amersham Pharmacia Biotech, Piscataway, N.J.). The pCANTAB 5E vector containing the anti-MUC-1 scFv were electroporated into TGi *E. coli*. ScFv were expressed in the TG1 *E. coli* and the 12E scFv was also expressed in HB2151 *E. coli*.

Anti-MUC-1 scfv Production.

ScFv were produced in cell culture plates for ELISA and competitive ELISA analysis. ScFv were grown overnight at 37° C. with shaking at 200 rpm in 2×YT medium containing 2.0% glucose and 100 µg/ml of ampicillin. Soluble scFv was produced by removal of glucose from the media and the addition of 1 mM of isopropyl-B-D-thiogalactopyranoside. ScFv expression was induced overnight at 30° C with shaking at 200 rpm. (Fisher Scientific, Pittsburgh, Pa.) (Sambrook). Soluble anti-MUC-1 scFv for scatchard and immunocytochemistry analysis was produced in 1 liter shaker flasks. ScFv obtained from a frozen glycerol stock was inoculated into 2×TY media containing 2% glucose and 100 µg/ml of ampicillin. The culture was grown for 8 hrs at 37° C., the bacteria was diluted 1:1000 using 2×TY media was containing 2% glucose and 100 µg/ml and grown an additional 16 hrs. The bacteria was pelleted by centrifugation at 6300 g for 15 minutes at 4° C. using a Sorval centrifuge with GSA rotor. Soluble scFv production was induced in 2×TY media containing 1 mM of IPTG and 100 µg/ml of ampicillin at 30° C. for 4.5 hrs. The bacterium was pelleted by centrifugation and stored at 20° C.

Anti-MUC-1 scFv DNA Sequence Analysis.

The anti-MUC-1 plasmids were extracted using the Qiafilter plasmid extraction kit and protocol. (Qiagen, Valencia, Calif.). The forward and reverse nucleotide sequences of the heavy and light chains of the anti-MUC-1 scFv were determined using the ABI Prism7 BigDye™ terminator cycle sequencing kit (PE Applied Biosystems, Foster City, Calif.) using the pCANTAB 5 sequencing primer S1 and S6 respectively (Amersham Pharmacia Biotech). An ABI model 377 automated sequencer (PE Applied Biosystems) was used for sequencing.

Affinity Purification.

ScFv was purified from the periplasm of the bacteria and used in Scatchard and immunocytochemistry analysis. The pelleted cells were removed from the −20° C. freezer and warmed slightly. The cells were suspended in 20 ml of TES [0.2 M Tris-HCL (pH 8.0), 0.5 mM EDTA, 0.5 M sucrose], 33 ml of 0.2×TES was added and the cells were incubated for 30 minutes on ice with moderate agitation. The cells were centrifuged as previously described; a 0.45 um filter was used to filter the supernatant. The anti-MUC-1 was purified from the supernatant by affinity column chromatography using the RPAS purification module (Amersham Pharmacia Biotech).

ELISA Analysis.

ELISA analysis was performed in triplicate. Incubations were carried out at 37EC for 1.5 hrs. Following each incubation, the plates were washed with phosphate buffered saline (PBS) [0.01 phosphate buffer, 0.0027 M potassium chloride and 0.137 M sodium chloride] pH 7.4 containing 0.5% Tween 20 followed by PBS washes alone. Pro-Bind™ ELISA assay plates (Becton Dickinson Labware, Franklin Lakes, N.J.) were coated overnight at room temperature with the MCF-7 cell lysate (200 µg/well) in 15 mM sodium bicarbonate buffer_ph 9.6. The ELISA plates were rinsed with PBS and blocked with PBS containing 3.0% dried non-fat milk for 1 hr. at room temperature. 10% bovine serum albumin (BSA) was used as a negative control. Tween 20 (10 µL) was added to the Pro-Bind plates followed by the addition of the anti-MUC-1 scFv (90 µL). The plate was washed then reacted with 100 µL of anti-E-tag diluted 1:250 in 3% non-fat milk solution. The plate was washed then developed using 2,2'-Amino-bis-3-ethylbenzthiazoline-6-sulfonic acid (ABTS) (Sigma-Aldrich, St. Louis, Mo.) containing 0.3% $H_2O_2$. The plate was read using a microplate reader at an absorbency of $A_{405}$ nM (Dynex, Chantilly, Va.).

Competitive ELISA.

Competitive ELISA analysis was performed in triplicate at each concentration. Incubations were carried out at 37EC for 1.5 hrs. Following each incubation, the plates were washed with PBS pH 7.4 containing 0.5% Tween 20 followed by PBS washes alone. Pro-Bind™ ELISA assay plates (Becton Dickinson Labware, Franklin Lakes, N.J.) were coated overnight at room temperature with the MCF-7 cell lysate (200 µg/well) in 15 mM sodium bicarbonate buffer pH 9.6. The ELISA plates were rinsed with PBS and blocked with PBS containing 3.0% dried non-fat milk for 1 hr. at room temperature. Ten percent bovine serum albumin (BSA) was used as a negative control. In a separate plate, soluble scFv containing 10% Tween 20 were prepared and stored on ice for 15 minutes. MCF-7 cell Tysate used as the competitor was diluted in 3% non-fat milk to provide the following concentrations 100 nM, 10 nM and 1 nM. The soluble scFv was transferred to the ELISA plate and incubated with the competitor. 100 µl of anti-E-tag diluted 1:250 in 3% non-fat milk solution was added to the wells and the plate incubated. The plate was developed with 2,2'-Aminobis-3-ethylbenzthiazoline-6-sulfonic acid (ABTS) (Sigma-Aldrich, St. Louis, Mo.) containing 0.3% $H_2O_2$. The plate was read using a microplate reader at an absorbency of $A_{405}$ nM (Dynex, Chantilly, Va.). Data was generated from three separate trials and analyzed.

ScFv Binding Affinities and Statistical Analysis.

Testing was performed using analysis of covariance. Statistically differences in slope among experiments were not significant; however, there were statistically significant differences among experiments in intercept.

$^{125}$I-anti-MUC-1 12E scFv.

The anti-MUC-1 12E scFv was iodinated using the Chloramine T labeling method (Schier et al. (1995) *Immunotechnology*, 1: 63–71). The specific activity of the $^{125}$I-anti-MUC-1 12E scFv was 0.46 mCi/mg.

High performance liquid chromatography was performed to purify the $^{125}$I-anti-MUC-1 12E scFv by applying 200 µl of the $^{125}$I-12E scFv onto a SEC-2000 column (Amersham Pharmacia) and collecting 0.5 ml fractions. $^{125}$I-12E scFv corresponded to 42 kD and 25 kD and were analyzed by Scatchard analysis.

Scatchard Analysis.

The ability of the 42 kD and 25 kD molecules to compete with $^{125}$I-12E scFv were assayed as follows. Assay solutions were prepared in triplicate using 5% BSA in PBS. $^{125}$I-12E (0.1 µg) was added to varying amounts of unlabeled immunoconjugate (0.5 µg, 1.0 µg, 2.0 µg and 5.0 µg); then MCF-7 cells ($5.0 \times 10^5$ cells) were added to a final volume of 0.15 ml. The solutions were gently vortexed and incubated at room temperature for 60 minutes. The solutions were centrifuged. The supernatant was carefully separated from the pelleted cells and transferred to a clean vial. The supernatant and pellets were counted using an LKB 1282 Compugamma CS well counter (Amersham-Pharmacia Biotech).

Production and Purification of Periplasmic scFv.

Soluble anti-MUC-1 scFv was produced in 1 liter shaker flasks. ScFv obtained from a frozen glycerol stock was innoculated into 2×TY media containing 2% glucose and 100 µg/ml of ampicillin. The culture was grown for 8 hrs. at 37° C., the bacteria was diluted 1:1000 with 2×TY media containing 2% glucose and 100 µg/ml and grown an additional 16 hrs. The bacteria was pelleted by centrifugation as previously described. To induce soluble scFv production the bacterium was suspended in 1 liter of 2×TY media was containing 1 mM of IPTG and 100 µg/ml of ampicillin. The scFv was induced to produce soluble scFv for 4.5 hrs. at 30° C. The bacterium was pelleted by centrifugation. The pelleted cells were suspended in 20 ml of TES [0.2 M Tris-HCL (pH 8.0), 0.5 mM EDTA, 0.5 M sucrose], 33 ml of 0.2×TES was added and the cells were incubated for 30 minutes on ice with moderate agitation. The cells were centrifuged as previously described; a 0.45 µm filter was used to filter the supernatant. The anti-MUC-1 was purified from the supernatant by affinity chromatography using the RPAS purification module (Amersham Pharmacia Biotech).

Molecular Modeling.

In the Protein Data Bank (PDB) there are several single chain Fv constructs with experimentally determined three-dimensional structures that are similar to the clone 12E sequence. From these, the structure of the murine single chain Fv antibody MFE-23 (PDB code: 1QOK) was selected as a template, since it had the closest sequence homology (73% identical residues) as well as an identical linker sequence connecting the variable heavy-chain and light-chain domains. Conformation for the conserved structural regions of clone 12E was assigned directly from the structural template.

The six hypervariable loops (H1–H3 and L1–L3), that are responsible for antigen-binding, were modeled using additional structural information from the PDB, as follows. First, the PDB was searched for loops structures that had high sequence similarity to these six loop regions in 12E. Four of the hypervariable loops (H2, L1–L3) were found to have similar conformations in both the original template (MFE-23) and the set of structures with the closest by sequence similarity to 12E. The structures of two of the loops (H1 and H3) in MFE-23 was different from the consensus structure observed by comparing corresponding loops that were the most similar by sequence to 12E. In those two cases the consensus structure was used to model the corresponding clone 12E H1 and H3 loops.

The structure of variable heavy-chain domain for the clone 3D was obtained using the same procedure applied to clone 12E. Estimation of secondary structure for the clone 3D C-terminal region was done using PsiPred. Model-building was performed using MODELLER, followed by model quality assessment with Procheck.

Immunocytochemistry.

Anti-MUC-1 purified scFv were reacted with the MUC-1 positive MCF-7 cells (ATTC) and Raji B-cell lymphoma cells. Cells were fixed for 5 minutes in ice-cold acetone. The cells were washed in PBS (Sigma-Aldrich). All incubations except were noted were for 1.5 hrs. at 37° C. in a humidified chamber. Following each incubation, the slides were washed 3 times for 3 minutes each in PBS. The slides were incubated with anti-MUC-1 scFv, Lym-1 monoclonal antibody (negative control) at a 1:1000 dilution or the anti-BrE-3 monoclonal antibody (positive control) at a 1:1000 dilution which recognizes the TRP amino acids sequence. The slides were incubated with either anti-E-tag monoclonal antibody (Amersham Pharmacia Biotech) at a 1:250 dilution or anti-Mouse Fc specific HRP conjugated IgG monoclonal antibody (Sigma-Aldrich) at a 1:1000 dilution. The slides incubated with the anti-E-tag monoclonal antibody were incubated with the anti-Mouse Fc specific HRP conjugated IgG monoclonal antibody at a 1:1000 dilution (Sigma-Aldrich). The slides were incubated with DAB [3,3'-Diaminobenzidine tetrahydrochloride] (Sigma-Aldrich) at room temperature for 30 minutes. The slides were counterstained using Harris Hematoxylin (Sigma-Aldrich). The slides were placed under running tap water until the water ran clear. The slides were dipped in differentiating solution [30 mM HCL in 70% ethanol], followed by a one minute incubation in a dilute alkaline solution (1.25 mM NaOH). The slides were dehydrated and mounted using Permount (Fisher Scientific). Photographs were obtained using the Provis Olympus microscope.

Results:

DNA Sequence Analysis

Automated DNA sequencing established that five of the seven scFv analyzed contained both the $V_H$ and $V_L$ sequence that forms the antigen binding site while 3D scFv contained only the $V_H$ chain sequence and 2B scFv contained only the $V_L$ (see, e.g. SEQ ID NOS:1–8, Table 1, and Sequence Listing).

ELISA Analysis.

Seven scFv were identified to be reactive with the MUC-1 antigen expressed on the surface of the MCF-7 breast adenocarcinoma. While the 2B scFv which contains only the $V_L$ immunoglobulin chain region was less reactive, the 3D scFv which contains only the $V_H$ immunoglobulin chain region was intensely reactive with the MUC-1 positive MCF-7 cells (Table 3, Sequence Listing) (Walsh et al. (2000) *Breast cancer research and treatment.* 58: 255–266).

Competitive ELISA Analysis.

Figure 1:
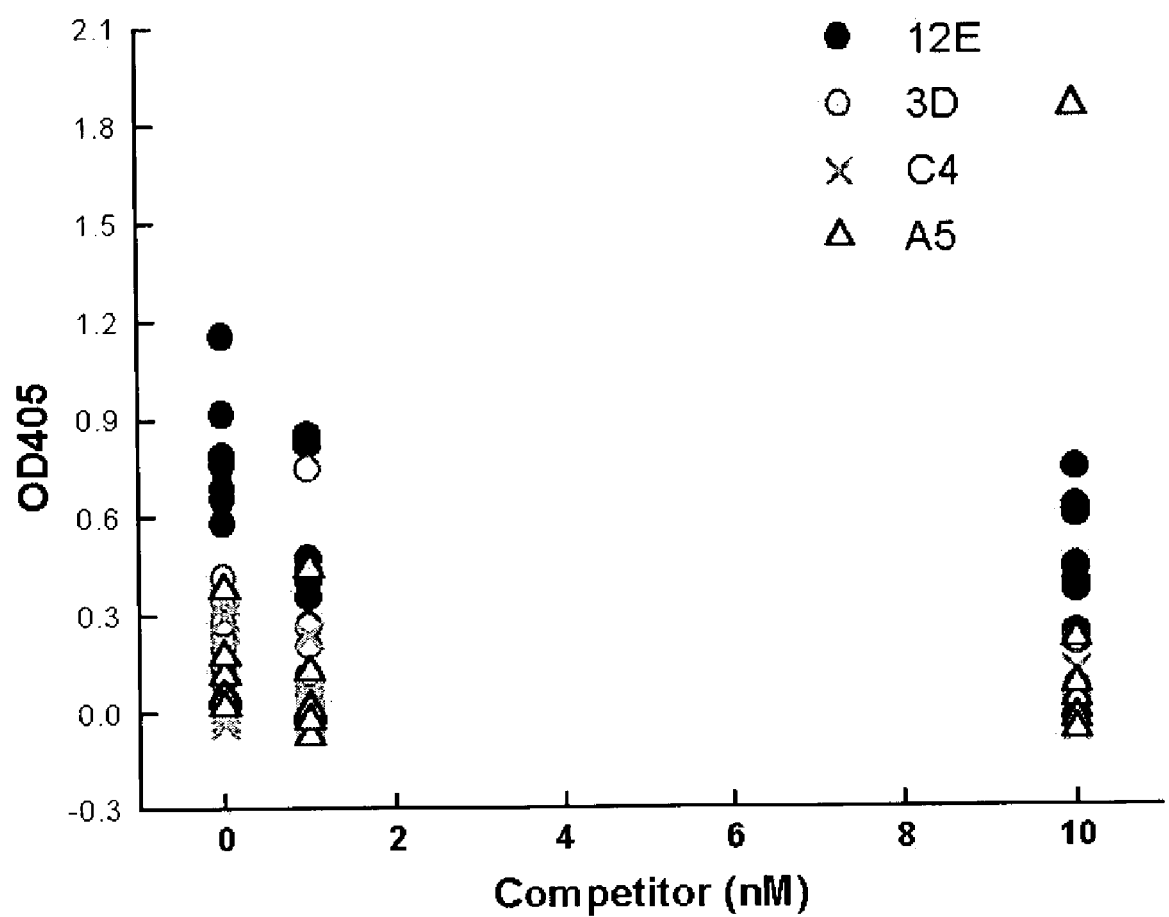
FIG. 1 shows the results of a competitive ELISA. Anti-MUC-1 scFv was strongly inhibited at the 1 nM with a slight increase in inhibition occurring with 10 nM concentrations of MUC-1 competitor. The greatest reduction in binding occurred with scFv A5 (Δ), C4 (X), 3D (○), and 12E (●), respectively.
Figure 2A:
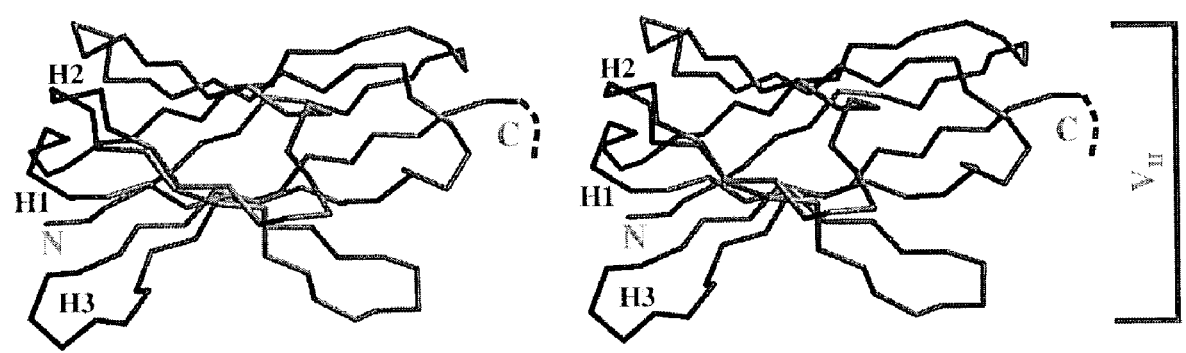
FIG. 2A shows a stereo representation (variant 1) of the three-dimensional model for clone 12E. Variable heavy chain ($V_H$) and light chain ($V_L$) domains are shown. Hypervariable antigen-binding lops are labeled (H1–H3) (L1–L3). The approximate path of Gly-Ser-rich connector between domains is indicated with a broken line.
Figure 2B:
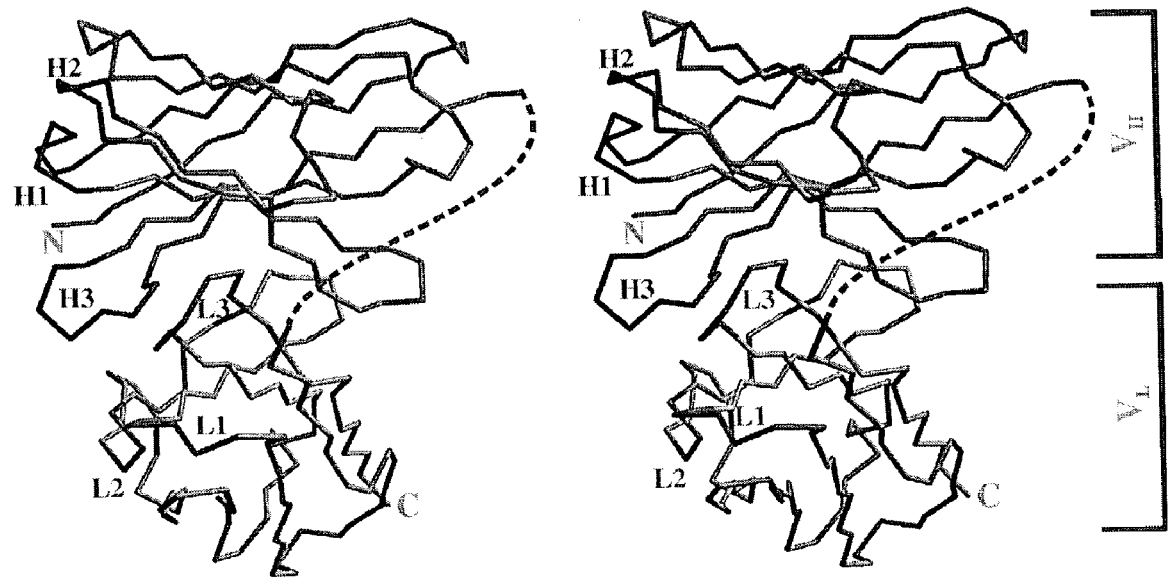
FIG. 2B shows a stereo representation (variant 1) of the three-dimensional model for the variable heavy-chain ($V_H$) domain of clone 12D. Notations are the same as in FIG. 2A.

Incubation with increasing amounts of the MUC-1 antigen as expressed on the MCF-7 cell membrane inhibited binding the subsequent of four of the seven scFv to the plated MUC-1 antigen FIG. 1. These scFv were substantially inhibited (by at least 50%) with only 1 nM of the competitor; a modest increase in inhibition occurred with 10 nM of the MUC-1 competitor. The four scFv were inhibited from subsequent binding with MUC-1 with 1 nM of competitor as follows: A5 (89%); C4 (94%), 3D (50%) and 12E (50%). Linear regression analysis of the ELISA data was used to calculate binding affinities. All four scFv chosen for analysis had $K_a$ of greater than $1.5 \times 10^8$. ScFv C4 ($K_a = 8.2 \times 10^8$) and A5 had similar affinities ($K_a = 7.1 \times 10^8$) with slightly lower affinities calculated for scFv 3D ($K_a = 2.2 \times 10^8$) and 12E ($K_a = 1.7 \times 10^8$).

Analysis of Affinity by ELISA.

The analysis consisted of data compiled from three separate experiments performed in triplicate. Overall the model for the 12E scFv indicates a statistically significant intercept ($p<0.001$) and slope ($p=0.04$). There appears to be a difference among the experiments in intercept ($p=0.1$). Affinity estimates range from $1.1 \times 10^8$ to $1.5 \times 10^7$ among experiments. Only experiment 1 was statistically significant on its own giving Analysis of the 3D scFv demonstrated a lower intercept than that obtained from 12E, but indicated of a statistically significant intercept ($p<0.001$) and slope ($p=0.04$). No indication of differences among experiments. Affinities ranged from 1.2 to $1.5 \times 10^8$. None of individual experiments were statistically significant on their own.

Analysis of the C4 scFv indicated experimental differences in intercept ($p=0.1$). The overall estimate of the intercept is statistically significant ($p=0.01$), but not as strong as for 12E or 3D. The slope is only marginally significant ($p=0.09$). For the individual experiments—the first 1 provided a positive estimate for the slope, so no affinity assessment could be made. There was no statistical significance. The second experiment was marginally statistically significant overall ($p=0.054$). Affinity estimate was $2.3 \times 10^8$. The 3rd experiment was also not statistically significant ($p=0.43$). Affinity estimate $1.01 \times 10^9$. Note that the affinity seems to be high just because the intercept is close to 0 so that little change has to occur to decrease the value by 50%.

Analysis of the A5 scFv indicated the model was not statistically significant and none of the individual experiments are statistically significant on their own. The intercepts were so small that it makes determination of affinity questionable. However, in experiment 3, again, the estimate for slope is positive.

Scatchard Analysis of the $^{125}$I-anti-MUC-1 12E scFv.

$^{125}$I-anti-MUC-1 12E scFv was used to confirm the binding affinity of this molecule compared to the previous analysis. Two fractions purified by HPLC were analyzed, a 42 kD fraction considered to be a diabody of (divalent) anti-MUC-1 12E scFv and a 25 kD fraction representative of monovalent anti-MUC-1 12E scFv. Scatchard analysis of the 42 kD fraction agreed superbly with the affinity ($Ka=1.7\pm0.24\times10^8$ M$^{-1}$) calculated by Linear regression analysis from the data produced by the competitive ELISA assay. The 25 kD fraction had an affinity of $8.6\pm1.1\times10^7$ M$^{-1}$ by Scatchard analysis.

Molecular Model.

A three-dimensional model for the clone 12E. The model includes two structural domains corresponding to the variable heavy-chain and light-chain domains. The linker between these domains was not explicitly modeled, since the crystallographic study of single chain $F_v$ antibody MFE-23 suggests that this linker is flexible and most likely does not assume a unique conformation. Short sequence fragments at the N- and C-terminus of clone 12E, extending beyond the structure of $V_H$ and $V_L$ domains are also expected to be flexible and were therefore not modeled. The modeled structure of clone 12E is very similar to that of MFE-23 including four out of six hypervariable antigen-binding loops. Two loops (H1 and H3) display marked differences from the MFE-23 template, and H3 loop has the most dissimilar conformation.

The clone 3D sequence includes a variable heavy-chain region and a Gly/Ser-rich linker, identical to those in clone 12E. However, instead of complete variable light-chain domain, the sequence of clone 3D following the linker is a composition of short subsequences of the N-terminal and C-terminal regions of light-chain domain. Since this short composite region is flanked by Gly/Ser-rich linker and the E-tag that are not expected to have rigid conformations, this region is unlikely to form stable three-dimensional structure. Secondary structure prediction for the clone 3D sequence suggests that at most this composite C-terminal region could form a β-hairpin.

Both the 12E and 3D clones bind the same antigen with almost identical affinity. At the same time, the C-terminal part of clone 3D, following Gly/Ser-rich linker, does not include any of the light-chain antigen-binding loops, and, as discussed above, also is not expected to form a stable three-dimensional structure. As can be seen from the structural model, the Gly/Ser-rich linker is on the other side of the heavy-chain domain hypervariable loops, making it unlikely that C-terminal part of clone 3D would affect the interaction of these loops with the antigen. Thus, these modeled structures, combined with the binding affinity measurements, strongly suggest that in both clones the antigen-binding is mediated only (or mostly) by heavy-chain antigen-binding loops (H1–H3). This is in good agreement with the antigen-binding mode suggested for MFE-23, based on the intermolecular packing in the crystal.

Immunocytochemistry

Figure 3:
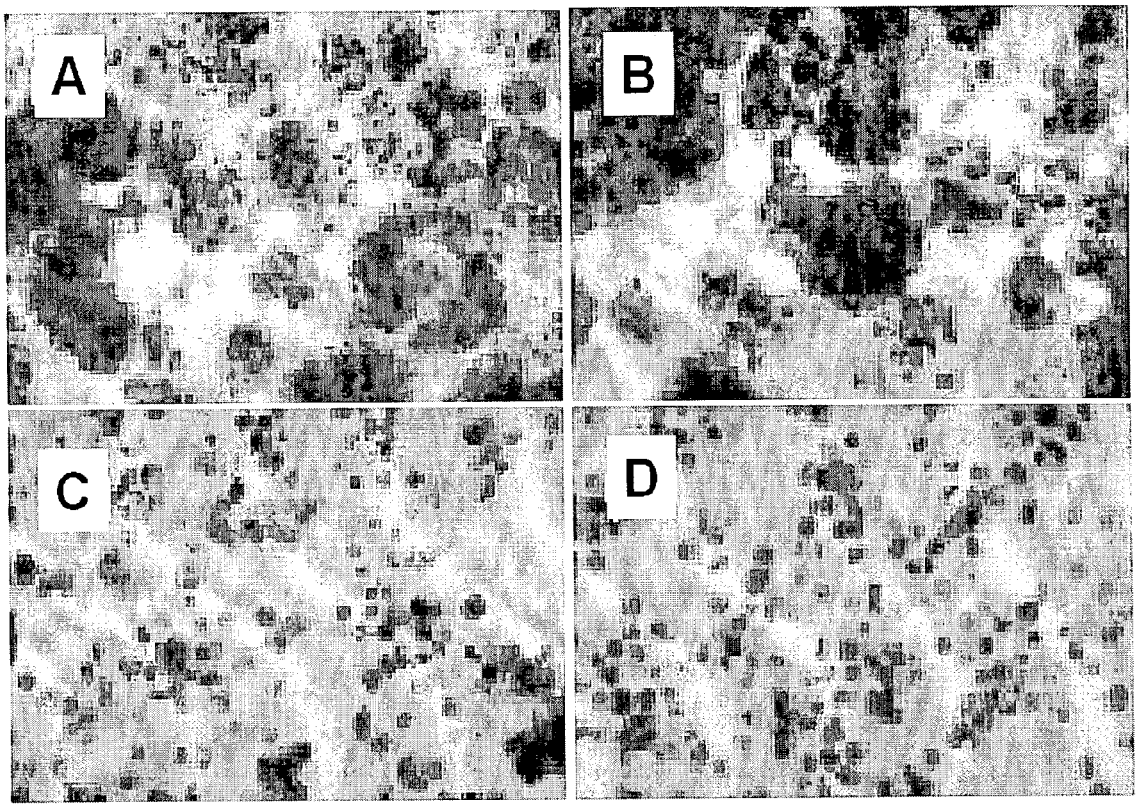
FIG. 3, panels A through D shows the results of anti-MUC-1 ScFv immunocytochemistry. The Anti-MUC-1 scFv 12E scFv reacts specifically with the MUC-1 membrane antigen expressed on MCF-7 breast adenocarcinoma cells. Panel A: BrE-3 monoclonal antibody reactive with MCF-7 cells (positive control). Panel B: Anti-MUC-1 scFv reactive with MCF-7 cells. Panel C: Lym-1 monoclonal antibody reactive with Raji B-cell lymphoma cells (positive control)

The anti-MUC-1 12E scFv was evaluated for reactivity with the MUC-1 membrane antigen expressed on the MCF-7 breast adenocarcinoma cells (FIG. 3, panel A). The 12 E scFv demonstrated highlyreactive binding far greater than 50% reactive with MCF-7 cells, but onlyminimally reactive with the Raji B-cell lymphoma cell line known to produce low amounts of MUC-1 (FIG. 3, panel B). Staining of the MCF-7 cells was heterogenous with both the cytoplasm and membrane observed with the anti-MUC-1 scFv. The staining pattern observed is characteristic of MUC-1 staining of breast adenocarcinomas (Walsh et al. (2000) *Breast Cancer Res. & Treatment*, 58: 255–266; Schumacher and Adam (1998) *Cytochemistry*, 46: 127–0134). The BrE-3 monoclonal antibody used as a positive control recognizes MUC-1 expressed on MCF-7 cells and the Lym-1 monoclonal antibody also used as the positive control recognizes the abundant HLA-DR10 variant antigen on Raji B-cell lymphoma cell line (FIG. 3, panel C and FIG. 3, panel D) (Howell et al. (1995) *Internat. J. Biol. Markers*, 10: 126–135).

Discussion.

Anti-MUC-1 scFv generated by genetic engineering and phage library technology have been isolated that recognize MUC-1 on human breast adenocarcinoma cells. Anti-MUC-1 scFv generated by genetic engineering and phage library technology have been isolated which recognize MUC-1 on human breast and adenocarcinoma cells. Competitive ELISA demonstrated that four of the seven scFv including 3, panel D, scFv ($V_L$ immunoglobulin chain region not present) were inhibited by the addition of increasing amounts of MUC-1 competitor (1 nm to 10 nm). Linear regression estimated that all four of the selected scFv had binding affinities ($K_a$) greater than $1.0 \times 10^8 M^{-1}$.

Sequencing results demonstrated that four of the seven scFv sequenced had intact $V_H$ and $V_L$ immunoglobulin regions containing amino acids likely involved in direct antigen contact as well as the structural amino acids necessary for the formation of the antigen binding pocket. Although the aim of this investigation was to characterize and select anti-MUC-1 scFv ($V_H$-linker-$V_L$) with the potential for clinical application, one of the scFv that has only the $V_L$ immunoglobulin region recognized the MUC-1 positive MCF-7 cells lysate determined by ELISA analysis whereas 3D scFv was reactive with the MCF-7 cell lysate by competitive ELISA as well as by direct cell staining even though this particular scFv lacks the $V_L$ antigen binding domain. This suggests that binding of 3D and 12E scFv, which have the same $V_H$ bind primarily by the interaction of amino acids contained within the $V_H$ immunoglobulin region with the MUC-1 antigen. The importance of $V_H$ immunoglobulin region binding to the antigen has been previously reported for antibodies and antibody fragments produced via immunization (Cai and Garen (1996) *Proc. Natl. Acad. Sci., USA*, 93: 6280–6285). X-ray crystallographic analysis of antibody-antigen complexes offers further validation of the importance of the heavy (H) chain in binding the antigen. (Padlan (1994) *Mo. Immunol.*, 31: 169–217). While binding to antigen in both disease and immunization seems primarily ascribed to $V_H$ immunoglobulin chain region, Song et al. (2000) *Biochem. Biophys. Res. Comm*, 268: 390–394, reported the principal role of $V_L$ in binding to the hepatitis B virus. Due to the limited number of scFv evaluated that lack the $V_L$ immunoglobulin region, we cannot rule out that scFv that recognize the MUC-1 antigen primarily through $V_L$ binding may exist within the library.

Heterogeneous MUC-1 expression on epithelial carcinoma has been well documented using monoclonal antibody. Hoogenboom et al. using an anti-MUC-1 scFv derived from a naive human phage library reported also reported heterogeneous. While the majority of monoclonal antibodies against MUC-1 recognize amino acids on the present in the glycosylation some of the monoclonal antibodies recognize carbohydrates a. Therefore for diagnosis or delivery of non-radioactive cytotoxic agents to malignant cells, a cocktail of anti-MUC-1 targeting molecules may be useful. In contrast, the use of anti-MUC-1 scFv in delivery of radiation to cells expressing MUC-1 could with the appropriate radionuclide allow adjacent cells to be lethally irradiated without direct binding.

ScFv for therapeutic application will likely best be utilized as components of molecules rather than as a single targeting agent. These scFv molecules initially envisioned and later demonstrated to have significantly increased tumor uptake and blood clearance compared to intact MoAbs have to disadvantage of rapid accumulation and elimination from the body by the kidneys due to their reduced size (Wu et al. (1996) *Immunotechnology*. 2: 21–36; Dall'Acqua and Carter (1998) *Curr. Opin. Struct. Biol.* 8: 443–450; Adams (1998) *In Vivo*, 12: 11–22; Yokota et al. (1992) *Cancer Res*, 52: 3402–3408; Begent et al. (1996) *Nat. Med*, 2: 979–984; DeNardo et al. (1999) *Clin Cancer Res*, 10: 3213–3218; Adams and Schier (1999) *J. Imm. Meth.*, 231: 249–260). ScFv can serve as the binding elements on a "platform" constructed of multi or bispecific agents, with one arm specific for binding the radioconjugate and the other a tumor antigen allowing the small radionuclide to administered after the tumor binding molecule has localized to the tumor and cleared from the circulation. Use of scFv or a portion of the scFv as a component presents the opportunity to assemble a tumor-seeking molecule with optimal clearance and tumor penetration.

TABLE 3

Reactivity of anti-MUC-1 scFv.

| Anti-MUC-1 scFv | ELISA Absorbance | Intact Sequence |
|---|---|---|
| 12E | +++ | Yes |
| A5 | + | Yes |
| C4 | + | Yes |
| 3D | +++ | No $V_L$ |
| 2B | + | No $V_H$ |
| E2 | ++ | Yes |

ScFv were random isolates from the anti-MUC-1 phage library identified by ELISA analysis. The MCF-7 cell line was used for screening the scFv for reactivity. The ELISA absorbance scales with background corrected are as follows: +++ > 0.5; ++ 0.25–0.5., − < 0.25.

Example 2

Immunohistopathology Staining in a Prostate Cancer

FIG. 4 illustrates staining of prostate cancer using three of the scFv described herein. The scFv is placed on the tissue on the slide and then washed off followed with a biotinylated anti mouse antibody for reaction with any bound scFv and then with a color reagent.

All studies here are on the same tumor for comparison. We also have found two of the scFv stained almost all of the 20 tumors present and very little on normal tissue in a tissue array.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated antibody that specifically binds MUC-1, said antibody comprising a domain comprising the amino acid sequence of a polypeptide selected from the group consisting of a 12E variable light domain (SEQ ID NO:2), an A5 variable light domain (SEQ ID NO:6), a C4 variable light domain (SEQ ID NO:8), a B5 variable light domain (SEQ ID NO:10), an E1 variable light domain (SEQ ID NO:12), a 12E variable heavy domain (SEQ ID NO:1), an A5 variable heavy domain (SEQ ID NO:5), a C4 variable heavy domain (SEQ ID NO:7), a B5 variable heavy domain (SEQ ID NO:9), and a E1 variable heavy domain (SEQ ID NO:11).

2. The antibody of claim 1, wherein said antibody is a single chain antibody.

3. The antibody of claim 1, wherein said antibody comprises:
a variable light domain selected from the group consisting of 12E variable light domain (SEQ ID NO:2), an A5 variable light domain (SEQ ID NO:6), a C4 variable light domain (SEQ ID NO:8), a B5 variable light domain (SEQ ID NO:10), and an E1 variable light domain (SEQ ID NO:12); and
a variable heavy domain selected from the group consisting of a a 12E variable heavy domain (SEQ ID NO:1), an A5 variable heavy domain (SEQ ID NO:5), a C4 variable heavy domain (SEQ ID NO:7), a B5 variable heavy domain (SEQ ID NO:9), and an E1 variable heavy domain (SEQ ID NO:11).

4. The antibody of claim 3, wherein said antibody comprises a 12E variable heavy domain (SEQ ID NO:1) and a 12E variable light domain (SEQ ID NO:2).

5. The antibody of claim 3, wherein said antibody comprises an A5 variable heavy domain (SEQ ID NO:5) and an A5 variable light domain (SEQ ID NO:6).

6. The antibody of claim 3, wherein said antibody comprises a C4 variable heavy domain (SEQ ID NO:7) and a C4 variable light domain (SEQ ID NO:8).

7. The antibody of claim 3, wherein said antibody comprises a B5 variable heavy domain (SEQ ID NO:9) and a B5 variable light domain (SEQ ID NO:10).

8. The antibody of claim 3, wherein said antibody comprises an E1 variable heavy main (SEQ ID NO:11) and an E1 variable light domain (SEQ ID NO:12).

9. The antibody of claim 3, wherein said antibody comprises a polypeptide selected from the group consisting of 12E (SEQ ID NO:15), A5 (SEQ ID NO:17), C4 (SEQ ID NO:18), B5 (SEQ ID NO:19), and E1 (SEQ ID NO:20).

10. The antibody of any one of claims 4, 5, 6, 7, 8, or 9, wherein said antibody is a single chain antibody.

11. The antibody of claim 10, wherein said antibody is an scfv antibody.

12. The antibody of any one of claims 4, 5, 6, 7, 8, or 9, wherein said antibody is a diabody.

13. The antibody of any one of claims 4, 5, 6, 7, 8, or 9, wherein said antibody is a humanized antibody.

14. antibody of any one of claims 4, 5, 6, 7, 8, or 9, wherein said antibody is a chimeric antibody.

15. A chimeric molecule comprising an antibody attached to an effector, wherein:
said antibody is an antibody that specifically binds MUC-1, said antibody comprising a domain comprising an amino acid sequence of a polypeptide selected from the group consisting of a 12E variable light domain (SEQ ID NO:2), an A5 variable light domain (SEQ ID NO:6), a C4 variable light domain (SEQ ID NO:8), a B5 variable light domain (SEQ ID NO:10), an E1 variable light domain (SEQ ID NO:12), a 12E variable heavy domain (SEQ ID NO:1), an A5 variable heavy domain (SEQ ID NO:5), a C4 variable heavy domain (SEQ ID NO:7), a B5 variable heavy domain (SEQ ID NO:9), and an E1 variable heavy domain (SEQ ID NO:11); and
said effector is selected from the group consisting of an epitope tag, a second antibody, a label, a cytotoxin, a liposome, a radionuclide, a drug, a prodrug, a liposome, and a chelate.

16. The chimeric molecule of claim 15, wherein said antibody is a single chain antibody.

17. The chimeric molecule of claim 15, wherein said antibody comprises:
a variable light domain selected from the group consisting of a a 12E variable light domain (SEQ ID NO:2), an A5 variable light domain (SEQ ID NO:6), a C4 variable light domain (SEQ ID NO:8), a B5 variable light domain (SEQ ID NO:10), and an E1 variable light domain (SEQ ID NO:12); and
a variable heavy domain selected from the group consisting of, a 12E variable heavy domain (SEQ ID NO:1), an A5 variable heavy domain (SEQ ID NO:5), a C4 variable heavy domain (SEQ ID NO:7), a B5 variable heavy domain (SEQ ID NO:9), and an E1 variable heavy domain (SEQ ID NO:11).

18. The chimeric molecule of claim 15, wherein said antibody comprises a 12E variable heavy domain (SEQ ID NO:1) and a 12E variable light domain (SEQ ID NO:2).

19. The chimeric molecule of claim 15, wherein said antibody comprises an A5 variable heavy domain (SEQ ID NO:5) and an A5 variable light domain (SEQ ID NO:6).

20. The chimeric molecule of claim 15, wherein said antibody comprises a C4 variable heavy domain (SEQ ID NO:7) and a C4 variable light domain (SEQ ID NO:8).

21. The chimeric molecule of claim 15, wherein said antibody comprises a B5 variable heavy domain (SEQ ID NO:9) and a B5 variable light domain (SEQ ID NO:10).

22. The chimeric molecule of claim 15, wherein said antibody comprises an E1 variable heavy domain (SEQ ID NO:11) and an E1 variable light domain (SEQ ID NO:12).

23. The chimeric molecule as in any one of claims 18, 19, 20, 21, and 22, wherein said antibody is a single chain antibody.

24. The chimeric molecule of claim 23, wherein said antibody is an scfv antibody.

25. The chimeric molecule of claim 23, wherein said effector is an epitope tag selected from the group consisting of an avidin, and a biotin.

26. The chimeric molecule of claim 23, wherein said effector is a cytotoxin selected from the group consisting of a *Diphtheria* toxin, a *Pseudomonas* exotoxin, a ricin, an abrin, and a thymidine kinase.

27. The chimeric molecule of claim 23, wherein said effector is a chelate comprising a metal isotope selected from the group consisting of of $^{99}$Tc, $^{203}$Pb, $^{67}$Ga, $^{68}$Ga, $^{72}$As, $^{111}$In, $^{113m}$In, $^{97}$Ru, $^{62}$Cu, $^{641}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag.

28. The chimeric molecule of claim 23, wherein said effector is a chelate comprising DOTA.

* * * * *

SEQUENCE LISTING

<160> NUMBER OF SEQ ID NOS: 22

<210> SEQ ID NO 1
<211> LENGTH: 119
<212> TYPE: PRT
<213> ORGANISM: Mus Musculus

<400> SEQUENCE: 1

Gln Val Lys Leu Gln Gln Ser Gly Thr Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Asp Ile Asp Trp Val Arg Gln Thr Pro Glu Gln Gly Leu Glu Trp Ile
        35                  40                  45

Gly Trp Ile Phe Pro Gly Glu Gly Ser Thr Glu Tyr Asn Glu Lys Phe
    50                  55                  60

Lys Gly Arg Ala Thr Leu Ser Val Asp Lys Ser Ser Ser Thr Ala Tyr
65                  70                  75                  80

Met Glu Leu Thr Arg Leu Thr Ser Glu Asp Ser Ala Val Tyr Phe Cys
                85                  90                  95

Ala Arg Gly Asp Tyr Tyr Arg Arg Tyr Phe Asp Leu Trp Gly Gln Gly
            100                 105                 110

Thr Thr Val Thr Val Ser Ser
        115

<210> SEQ ID NO 2
<211> LENGTH: 110
<212> TYPE: PRT
<213> ORGANISM: Mus Musculus

<400> SEQUENCE: 2

Asp Ile Glu Leu Thr Gln Ser Pro Ala Ile Met Ser Ala Ser Pro Gly
1               5                   10                  15

Glu Arg Val Thr Met Thr Cys Ser Ala Ser Ser Ser Ile Arg Tyr Ile
            20                  25                  30

Tyr Trp Tyr Gln Gln Lys Pro Gly Ser Ser Pro Arg Leu Leu Ile Tyr
        35                  40                  45

Asp Thr Ser Asn Val Ala Pro Gly Val Pro Phe Arg Phe Ser Gly Ser
    50                  55                  60

Gly Ser Gly Thr Ser Tyr Ser Leu Thr Ile Asn Arg Met Glu Ala Glu
65                  70                  75                  80

Asp Ala Ala Thr Tyr Tyr Cys Gln Glu Trp Ser Gly Tyr Pro Tyr Thr
                85                  90                  95

Phe Gly Gly Gly Thr Lys Leu Glu Leu Lys Arg Ala Ala Ala
            100                 105                 110

<210> SEQ ID NO 3
<211> LENGTH: 119
<212> TYPE: PRT
<213> ORGANISM: Mus Musculus

<400> SEQUENCE: 3

Gln Val Lys Leu Gln Glu Ser Gly Pro Glu Val Val Lys Pro Gly Ala
1               5                   10                  15

Ser Val Lys Leu Ser Cys Lys Ala Ser Gly Tyr Ile Phe Thr Ser Tyr
            20                  25                  30

-continued

Asp Ile Asp Trp Val Arg Gln Thr Pro Glu Gln Gly Leu Glu Trp Ile
            35                  40                  45

Gly Trp Ile Phe Pro Gly Glu Gly Ser Thr Glu Tyr Asn Glu Lys Phe
        50                  55                  60

Lys Gly Arg Ala Thr Leu Ser Val Asp Lys Ser Ser Thr Ala Tyr
65                  70                  75                  80

Met Glu Leu Thr Arg Leu Thr Ser Glu Asp Ser Ala Val Tyr Phe Cys
                85                  90                  95

Ala Arg Gly Asp Tyr Tyr Arg Arg Tyr Phe Asp Leu Trp Gly Gln Gly
            100                 105                 110

Thr Thr Val Thr Val Ser Ser
        115

<210> SEQ ID NO 4
<211> LENGTH: 23
<212> TYPE: PRT
<213> ORGANISM: Mus Musculus

<400> SEQUENCE: 4

Asp Ile Glu Leu Thr Gln Ser Pro Gly Val Lys Thr Gly Thr Lys Leu
1               5                   10                  15

Glu Leu Lys Arg Ala Ala Ala
            20

<210> SEQ ID NO 5
<211> LENGTH: 112
<212> TYPE: PRT
<213> ORGANISM: Mus Musculus

<400> SEQUENCE: 5

Gln Val Lys Leu Gln Gln Ser Gly Pro Gly Leu Cys Ser Pro His Arg
1               5                   10                  15

Ala Cys Pro Ser Pro Ala Gln Pro Leu Val Ser His Leu Leu Met Val
            20                  25                  30

Tyr Ile Gly Phe Ala Ser Leu Gln Glu Arg Val Trp Ser Gly Trp Glu
        35                  40                  45

Tyr Gly Val Val Glu Ala Gln Thr Ile Ile Gln Leu Ser Tyr Pro Asp
    50                  55                  60

Thr Ser Thr Arg Thr Thr Pro Arg Ala Lys Phe Ser Leu Lys Trp Thr
65                  70                  75                  80

Val Tyr Asn Leu Met Thr Glu Ala Tyr Thr Thr Val Gly Val Met Gly
                85                  90                  95

Thr Ser Leu Thr Pro Gly Ala Asn Gly Thr Thr Val Thr Val Ser Ser
            100                 105                 110

<210> SEQ ID NO 6
<211> LENGTH: 111
<212> TYPE: PRT
<213> ORGANISM: Mus Musculus

<400> SEQUENCE: 6

Asp Ile Ser Ser Leu Ser Leu Gln Leu Pro Leu Tyr Leu Trp Gly Arg
1               5                   10                  15

Gly Pro Pro Ser His Thr Gly Pro Ala Lys Val Ser Val His Leu Ala
            20                  25                  30

Ile Val Ile Cys Thr Gly Thr Asn Arg Asn Gln Asp Ser His Pro Asp
        35                  40                  45

Ser Ser Ser Ile Leu Tyr Pro Thr Ile Trp Gly Pro Cys Gln Val Gln

```
              50                  55                  60
Trp Gln Trp Val Trp Asp Arg Leu His Pro Gln His Pro Ser Cys Gly
 65                  70                  75                  80

Gly Arg Gly Cys Leu Gln Pro Ile Thr Val Ser Thr Leu Gly Ala Tyr
                 85                  90                  95

Thr Phe Gly Gly Gly Thr Lys Leu Glu Leu Lys Arg Ala Ala Ala
                100                 105                 110

<210> SEQ ID NO 7
<211> LENGTH: 116
<212> TYPE: PRT
<213> ORGANISM: Mus Musculus

<400> SEQUENCE: 7

Gln Val Gln Leu Gln Glu Ser Gly Pro Gly Leu Val Gln Pro Ser Gln
  1               5                  10                  15

Ser Leu Ser Ile Thr Cys Thr Val Ser Gly Phe Ser Leu Thr Ala Tyr
                 20                  25                  30

Gly Val His Trp Ile Arg Gln Ser Pro Gly Lys Gly Leu Glu Trp Leu
                 35                  40                  45

Gly Val Ile Trp Ser Gly Gly Thr Asp Tyr Asn Pro Ala Phe Ile
             50                  55                  60

Ser Arg Leu Asn Ile Asn Lys Asp Asn Ser Lys Ser Gln Val Phe Phe
 65                  70                  75                  80

Lys Val Asp Ser Leu Gln Leu Asp Asp Arg Gly Ile Tyr Tyr Cys Val
                 85                  90                  95

Arg Arg Asn Gly Tyr Phe Phe Asp Ser Trp Gly Gln Gly Thr Thr Val
                100                 105                 110

Thr Val Ser Ser
        115

<210> SEQ ID NO 8
<211> LENGTH: 130
<212> TYPE: PRT
<213> ORGANISM: Mus Musculus

<400> SEQUENCE: 8

Asp Ile Glu Leu Thr Gln Ser Pro Ala Ser Leu Leu Cys Leu Trp Gly
  1               5                  10                  15

Arg Gly Pro Pro Ser His Ala Gly Pro Thr Met Val Val Ser Thr Ser
                 20                  25                  30

Gly Tyr Asn Phe Ile Tyr Trp Ser Gln Gln Lys Pro Gly Gln Ser Pro
                 35                  40                  45

Lys Leu Leu Ile Tyr Leu Ser Ser Asn Leu Glu Ser Gly Val Pro Ala
             50                  55                  60

Arg Val Ser Gly Ser Gly Ser Arg Thr Tyr Phe Thr Leu Asn Ile His
 65                  70                  75                  80

Pro Val Glu Glu Glu Asp Ala Ala Thr Phe Tyr Cys Arg His Thr Arg
                 85                  90                  95

Glu Leu Pro Cys Thr Phe Gly Gly Arg Thr Lys Leu Glu Ile Lys Arg
                100                 105                 110

Ala Ala Ala Gly Ala Pro Val Pro Tyr Pro Asp Pro Leu Glu Pro Arg
            115                 120                 125

Ala Ala
    130
```

```
<210> SEQ ID NO 9
<211> LENGTH: 118
<212> TYPE: PRT
<213> ORGANISM: Mus Musculus

<400> SEQUENCE: 9

Gln Val Lys Leu Gln Glu Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Thr Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Asp Gly Tyr Tyr Ala Trp Phe Ala Tyr Trp Gly Gln Gly Thr
            100                 105                 110

Thr Val Thr Val Ser Ser
        115

<210> SEQ ID NO 10
<211> LENGTH: 110
<212> TYPE: PRT
<213> ORGANISM: Mus Musculus

<400> SEQUENCE: 10

Asp Ile Glu Leu Thr Gln Ser Pro Ala Ile Met Ser Ala Ser Pro Gly
1               5                   10                  15

Glu Arg Val Thr Met Thr Cys Ser Ala Ser Ser Ser Ile Arg Tyr Ile
            20                  25                  30

Tyr Trp Tyr Gln Gln Lys Pro Gly Ser Ser Pro Arg Leu Leu Ile Tyr
        35                  40                  45

Asp Thr Ser Asn Val Ala Pro Gly Val Pro Phe Arg Phe Ser Gly Ser
    50                  55                  60

Gly Ser Gly Thr Ser Tyr Ser Leu Thr Ile Asn Arg Met Glu Ala Glu
65                  70                  75                  80

Asp Ala Ala Thr Tyr Tyr Cys Gln Glu Trp Ser Gly Tyr Pro Tyr Thr
                85                  90                  95

Phe Gly Gly Gly Thr Lys Leu Glu Leu Lys Arg Ala Ala Ala
            100                 105                 110

<210> SEQ ID NO 11
<211> LENGTH: 118
<212> TYPE: PRT
<213> ORGANISM: Mus Musculus

<400> SEQUENCE: 11

Gln Val Lys Leu Gln Gln Ser Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Gly Gln Gly Leu Glu Trp Ile
        35                  40                  45

Gly Met Ile Asp Pro Ser Asp Ser Glu Thr His Tyr Asn Gln Met Phe
    50                  55                  60
```

```
Lys Asp Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Asp Gly Ser Ser Ser Trp Phe Ala Tyr Trp Gly Gln Gly Thr
            100                 105                 110

Thr Val Thr Val Ser Ser
        115

<210> SEQ ID NO 12
<211> LENGTH: 110
<212> TYPE: PRT
<213> ORGANISM: Mus Musculus

<400> SEQUENCE: 12

Asp Ile Glu Leu Thr Gln Ser Pro Ala Ile Met Ser Ala Ser Pro Gly
 1               5                  10                  15

Glu Arg Val Thr Met Thr Cys Ser Ala Ser Ser Ser Ile Arg Tyr Ile
             20                  25                  30

Tyr Trp Tyr Gln Gln Lys Pro Gly Ser Ser Pro Arg Leu Leu Ile Tyr
         35                  40                  45

Asp Thr Ser Asn Val Ala Pro Gly Val Pro Phe Arg Phe Ser Gly Ser
     50                  55                  60

Gly Ser Gly Thr Ser Tyr Ser Leu Thr Ile Asn Arg Met Glu Ala Glu
 65                  70                  75                  80

Asp Ala Ala Thr Tyr Tyr Cys Gln Glu Trp Ser Gly Tyr Pro Tyr Thr
                 85                  90                  95

Phe Gly Gly Gly Thr Lys Leu Glu Ile Lys Arg Ala Ala Ala
            100                 105                 110

<210> SEQ ID NO 13
<211> LENGTH: 118
<212> TYPE: PRT
<213> ORGANISM: Mus Musculus

<400> SEQUENCE: 13

Gln Val Lys Leu Gln Glu Ser Gly Ala Glu Leu Val Arg Pro Gly Ala
 1               5                  10                  15

Ser Val Lys Leu Ser Cys Lys Ala Ser Gly Tyr Ser Phe Thr Ser Tyr
             20                  25                  30

Trp Met Asn Trp Val Lys Gln Arg Pro Gly Gln Gly Leu Glu Trp Ile
         35                  40                  45

Gly Met Ile His Pro Ser Asp Ser Glu Thr His Tyr Asn Gln Met Phe
     50                  55                  60

Lys Asp Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Asp Gly Ser Ser Ser Trp Phe Ala Tyr Trp Gly Gln Gly Thr
            100                 105                 110

Thr Val Thr Val Ser Ser
        115

<210> SEQ ID NO 14
<211> LENGTH: 27
<212> TYPE: PRT
<213> ORGANISM: Mus Musculus
```

```
<400> SEQUENCE: 14

Asp Ile Glu Leu Thr Gln Ser Pro Ile Gly Gln Val Gly Asn Lys Thr
1               5                   10                  15

Gly Pro Lys Leu Glu Ile Lys Arg Ala Ala Ala
            20                  25

<210> SEQ ID NO 15
<211> LENGTH: 281
<212> TYPE: PRT
<213> ORGANISM: Mus Musculus

<400> SEQUENCE: 15

Val Lys Lys Leu Leu Phe Ala Ile Pro Leu Val Val Pro Phe Tyr Ala
1               5                   10                  15

Ala Gln Pro Ala Met Ala Gln Val Lys Leu Gln Gln Ser Gly Thr Glu
            20                  25                  30

Val Val Lys Pro Gly Ala Ser Val Lys Leu Ser Cys Lys Ala Ser Gly
        35                  40                  45

Tyr Ile Phe Thr Ser Tyr Asp Ile Asp Trp Val Arg Gln Thr Pro Glu
    50                  55                  60

Gln Gly Leu Glu Trp Ile Gly Trp Ile Phe Pro Gly Glu Gly Ser Thr
65                  70                  75                  80

Glu Tyr Asn Glu Lys Phe Lys Gly Arg Ala Thr Leu Ser Val Asp Lys
                85                  90                  95

Ser Ser Ser Thr Ala Tyr Met Glu Leu Thr Arg Leu Thr Ser Glu Asp
            100                 105                 110

Ser Ala Val Tyr Phe Cys Ala Arg Gly Asp Tyr Tyr Arg Arg Tyr Phe
        115                 120                 125

Asp Leu Trp Gly Gln Gly Thr Thr Val Thr Val Ser Ser Arg Gly Gly
    130                 135                 140

Gly Ser Gly Gly Gly Ser Gly Gly Gly Ser Asp Ile Glu Leu
145                 150                 155                 160

Thr Gln Ser Pro Ala Ile Met Ser Ala Ser Pro Gly Glu Arg Val Thr
                165                 170                 175

Met Thr Cys Ser Ala Ser Ser Ile Arg Tyr Ile Tyr Trp Tyr Gln
            180                 185                 190

Gln Lys Pro Gly Ser Ser Pro Arg Leu Leu Ile Tyr Asp Thr Ser Asn
        195                 200                 205

Val Ala Pro Gly Val Pro Phe Arg Phe Ser Gly Ser Gly Ser Gly Thr
    210                 215                 220

Ser Tyr Ser Leu Thr Ile Asn Arg Met Glu Ala Glu Asp Ala Ala Thr
225                 230                 235                 240

Tyr Tyr Cys Gln Glu Trp Ser Gly Tyr Pro Tyr Thr Phe Gly Gly Gly
                245                 250                 255

Thr Lys Leu Glu Leu Lys Arg Ala Ala Ala Gly Ala Pro Val Pro Tyr
            260                 265                 270

Pro Asp Pro Leu Glu Pro Arg Ala Ala
        275                 280

<210> SEQ ID NO 16
<211> LENGTH: 194
<212> TYPE: PRT
<213> ORGANISM: Mus Musculus

<400> SEQUENCE: 16
```

```
Val Lys Lys Leu Leu Phe Ala Ile Pro Leu Val Val Pro Phe Tyr Ala
1               5                   10                  15

Ala Gln Pro Ala Met Ala Gln Val Lys Leu Gln Glu Ser Gly Pro Glu
            20                  25                  30

Val Val Lys Pro Gly Ala Ser Val Lys Leu Ser Cys Lys Ala Ser Gly
        35                  40                  45

Tyr Ile Phe Thr Ser Tyr Asp Ile Asp Trp Val Arg Gln Thr Pro Glu
    50                  55                  60

Gln Gly Leu Glu Trp Ile Gly Trp Ile Phe Pro Gly Glu Gly Ser Thr
65                  70                  75                  80

Glu Tyr Asn Glu Lys Phe Lys Gly Arg Ala Thr Leu Ser Val Asp Lys
                85                  90                  95

Ser Ser Ser Thr Ala Tyr Met Glu Leu Thr Arg Leu Thr Ser Glu Asp
            100                 105                 110

Ser Ala Val Tyr Phe Cys Ala Arg Gly Asp Tyr Tyr Arg Arg Tyr Phe
        115                 120                 125

Asp Leu Trp Gly Gln Gly Thr Thr Val Thr Val Ser Ser Gly Gly Gly
    130                 135                 140

Gly Ser Gly Gly Gly Gly Ser Gly Gly Gly Gly Ser Asp Ile Glu Leu
145                 150                 155                 160

Thr Gln Ser Pro Gly Val Lys Thr Gly Thr Lys Leu Glu Leu Lys Arg
                165                 170                 175

Ala Ala Ala Gly Ala Pro Val Pro Tyr Pro Asp Pro Leu Glu Pro Arg
            180                 185                 190

Ala Ala

<210> SEQ ID NO 17
<211> LENGTH: 275
<212> TYPE: PRT
<213> ORGANISM: Mus Musculus

<400> SEQUENCE: 17

Val Lys Lys Leu Leu Phe Ala Ile Pro Leu Val Val Pro Phe Tyr Ala
1               5                   10                  15

Ala Gln Pro Ala Met Ala Gln Val Lys Leu Gln Gln Ser Gly Pro Gly
            20                  25                  30

Leu Cys Ser Pro His Arg Ala Cys Pro Ser Pro Ala Gln Pro Leu Val
        35                  40                  45

Ser His Leu Leu Met Val Tyr Ile Gly Phe Ala Ser Leu Gln Glu Arg
    50                  55                  60

Val Trp Ser Gly Trp Glu Tyr Gly Val Val Glu Ala Gln Thr Ile Ile
65                  70                  75                  80

Gln Leu Ser Tyr Pro Asp Thr Ser Thr Arg Thr Thr Pro Arg Ala Lys
                85                  90                  95

Phe Ser Leu Lys Trp Thr Val Tyr Asn Leu Met Thr Glu Ala Tyr Thr
            100                 105                 110

Thr Val Gly Val Met Gly Thr Ser Leu Thr Pro Gly Ala Asn Gly Thr
        115                 120                 125

Thr Val Thr Val Ser Ser Gly Gly Gly Ser Gly Gly Gly Gly Ser
    130                 135                 140

Gly Gly Gly Gly Ser Asp Ile Ser Ser Leu Ser Gln Leu Pro Leu
145                 150                 155                 160

Tyr Leu Trp Gly Arg Gly Pro Pro Ser His Thr Gly Pro Ala Lys Val
                165                 170                 175
```

```
Ser Val His Leu Ala Ile Val Ile Cys Thr Gly Thr Asn Arg Asn Gln
            180                 185                 190

Asp Ser His Pro Asp Ser Ser Ile Leu Tyr Pro Thr Ile Trp Gly
        195                 200                 205

Pro Cys Gln Val Gln Trp Gln Trp Val Trp Asp Arg Leu His Pro Gln
    210                 215                 220

His Pro Ser Cys Gly Gly Arg Gly Cys Leu Gln Pro Ile Thr Val Ser
225                 230                 235                 240

Thr Leu Gly Ala Tyr Thr Phe Gly Gly Thr Lys Leu Glu Leu Lys
                245                 250                 255

Arg Ala Ala Ala Gly Ala Pro Val Pro Tyr Pro Asp Pro Leu Glu Pro
            260                 265                 270

Arg Ala Ala
        275

<210> SEQ ID NO 18
<211> LENGTH: 260
<212> TYPE: PRT
<213> ORGANISM: Mus Musculus

<400> SEQUENCE: 18

Gln Val Gln Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Ala Tyr
            20                  25                  30

Gly Val His Trp Ile Arg Gln Ser Pro Gly Lys Gly Leu Glu Trp Leu
        35                  40                  45

Gly Val Ile Trp Ser Gly Gly Gly Thr Asp Tyr Asn Pro Ala Phe Ile
    50                  55                  60

Ser Arg Leu Asn Ile Asn Lys Asp Asn Ser Lys Ser Gln Val Phe Phe
65                  70                  75                  80

Lys Val Asp Ser Leu Gln Leu Asp Asp Arg Gly Ile Tyr Tyr Cys Val
                85                  90                  95

Arg Arg Asn Gly Tyr Phe Phe Asp Ser Trp Gly Gln Gly Thr Thr Val
            100                 105                 110

Thr Val Ser Ser Gly Arg Phe Ser Gly Gly Gly Ser Gly Gly Gly
        115                 120                 125

Gly Ser Asp Ile Glu Leu Thr Gln Ser Pro Ala Ser Leu Leu Cys Leu
    130                 135                 140

Trp Gly Arg Gly Pro Pro Ser His Ala Gly Pro Thr Met Val Val Ser
145                 150                 155                 160

Thr Ser Gly Tyr Asn Phe Ile Tyr Trp Ser Gln Gln Lys Pro Gly Gln
                165                 170                 175

Ser Pro Lys Leu Leu Ile Tyr Leu Ser Ser Asn Leu Glu Ser Gly Val
            180                 185                 190

Pro Ala Arg Val Ser Gly Ser Gly Ser Arg Thr Tyr Phe Thr Leu Asn
        195                 200                 205

Ile His Pro Val Glu Glu Glu Asp Ala Ala Thr Phe Tyr Cys Arg His
    210                 215                 220

Thr Arg Glu Leu Pro Cys Thr Phe Gly Gly Arg Thr Lys Leu Glu Ile
225                 230                 235                 240

Lys Arg Ala Ala Ala Gly Ala Pro Val Pro Tyr Pro Asp Pro Leu Glu
                245                 250                 255

Pro Arg Ala Ala
        260
```

<210> SEQ ID NO 19
<211> LENGTH: 260
<212> TYPE: PRT
<213> ORGANISM: Mus Musculus

<400> SEQUENCE: 19

```
Met Ala Gln Val Lys Leu Gln Glu Ser Gly Ala Glu Leu Val Arg Pro
1               5                   10                  15

Gly Ala Ser Val Thr Leu Ser Cys Lys Ala Ser Gly Tyr Thr Phe Thr
            20                  25                  30

Asp Tyr Glu Met His Trp Val Lys Gln Thr Pro Val His Gly Leu Glu
        35                  40                  45

Trp Ile Gly Ala Ile Asp Pro Glu Thr Gly Gly Thr Ala Tyr Asn Gln
    50                  55                  60

Lys Phe Lys Gly Lys Ala Thr Leu Thr Ala Asp Lys Ser Ser Ser Thr
65                  70                  75                  80

Ala Tyr Met Glu Leu Arg Ser Leu Thr Ser Glu Asp Ser Ala Val Tyr
                85                  90                  95

Tyr Cys Thr Arg Asp Gly Tyr Tyr Ala Trp Phe Ala Tyr Trp Gly Gln
            100                 105                 110

Gly Thr Thr Val Thr Val Ser Ser Gly Gly Gly Gly Leu Gly Gly Gly
        115                 120                 125

Gly Ser Gly Gly Gly Gly Ser Asp Ile Glu Leu Thr Gln Ser Pro Ala
    130                 135                 140

Ile Met Ser Ala Ser Pro Gly Glu Arg Val Thr Met Thr Cys Ser Ala
145                 150                 155                 160

Ser Ser Ser Ile Arg Tyr Ile Tyr Trp Tyr Gln Gln Lys Pro Gly Ser
                165                 170                 175

Ser Pro Arg Leu Leu Ile Tyr Asp Thr Ser Asn Val Ala Pro Gly Val
            180                 185                 190

Pro Phe Arg Phe Ser Gly Ser Gly Ser Gly Thr Ser Tyr Ser Leu Thr
        195                 200                 205

Ile Asn Arg Met Glu Ala Glu Asp Ala Ala Thr Tyr Tyr Cys Gln Glu
    210                 215                 220

Trp Ser Gly Tyr Pro Tyr Thr Phe Gly Gly Gly Thr Lys Leu Glu Leu
225                 230                 235                 240

Lys Arg Ala Ala Ala Gly Ala Pro Val Pro Tyr Pro Asp Pro Leu Glu
                245                 250                 255

Pro Arg Ala Ala
            260
```

<210> SEQ ID NO 20
<211> LENGTH: 260
<212> TYPE: PRT
<213> ORGANISM: Mus Musculus

<400> SEQUENCE: 20

```
Met Ala Gln Val Lys Leu Gln Gln Ser Gly Ala Glu Leu Val Arg Pro
1               5                   10                  15

Gly Ala Ser Val Lys Leu Ser Cys Lys Ala Ser Gly Tyr Thr Phe Thr
            20                  25                  30

Ser Tyr Trp Met Asn Trp Val Lys Gln Arg Pro Gly Gln Gly Leu Glu
        35                  40                  45

Trp Ile Gly Met Ile Asp Pro Ser Asp Ser Glu Thr His Tyr Asn Gln
    50                  55                  60
```

```
Met Phe Lys Asp Lys Ala Thr Leu Thr Val Asp Lys Ser Ser Ser Thr
 65                  70                  75                  80

Ala Tyr Met Gln Leu Ser Ser Leu Thr Ser Glu Asp Ser Ala Val Tyr
                 85                  90                  95

Tyr Cys Ala Arg Asp Gly Ser Ser Trp Phe Ala Tyr Trp Gly Gln
            100                 105                 110

Gly Thr Thr Val Thr Val Ser Ser Gly Gly Gly Ser Gly Gly Gly
            115                 120                 125

Gly Ser Gly Gly Gly Ser Asp Ile Glu Leu Thr Gln Ser Pro Ala
130                 135                 140

Ile Met Ser Ala Ser Pro Gly Glu Arg Val Thr Met Thr Cys Ser Ala
145                 150                 155                 160

Ser Ser Ser Ile Arg Tyr Ile Tyr Trp Tyr Gln Gln Lys Pro Gly Ser
                165                 170                 175

Ser Pro Arg Leu Leu Ile Tyr Asp Thr Ser Asn Val Ala Pro Gly Val
            180                 185                 190

Pro Phe Arg Phe Ser Gly Ser Gly Ser Gly Thr Ser Tyr Ser Leu Thr
            195                 200                 205

Ile Asn Arg Met Glu Ala Glu Asp Ala Ala Thr Tyr Tyr Cys Gln Glu
210                 215                 220

Trp Ser Gly Tyr Pro Tyr Thr Phe Gly Gly Gly Thr Lys Leu Glu Ile
225                 230                 235                 240

Lys Arg Ala Ala Ala Gly Ala Pro Val Pro Tyr Pro Asp Pro Leu Glu
                245                 250                 255

Pro Arg Ala Ala
            260

<210> SEQ ID NO 21
<211> LENGTH: 177
<212> TYPE: PRT
<213> ORGANISM: Mus Musculus

<400> SEQUENCE: 21

Met Ala Gln Val Lys Leu Gln Glu Ser Gly Ala Glu Leu Val Arg Pro
 1               5                  10                  15

Gly Ala Ser Val Lys Leu Ser Cys Lys Ala Ser Gly Tyr Ser Phe Thr
                20                  25                  30

Ser Tyr Trp Met Asn Trp Val Lys Gln Arg Pro Gly Gln Gly Leu Glu
            35                  40                  45

Trp Ile Gly Met Ile His Pro Ser Asp Ser Glu Thr His Tyr Asn Gln
 50                  55                  60

Met Phe Lys Asp Lys Ala Thr Leu Thr Val Asp Lys Ser Ser Ser Thr
 65                  70                  75                  80

Ala Tyr Met Gln Leu Ser Ser Leu Thr Ser Glu Asp Ser Ala Val Tyr
                 85                  90                  95

Tyr Cys Ala Arg Asp Gly Ser Ser Trp Phe Ala Tyr Trp Gly Gln
            100                 105                 110

Gly Thr Thr Val Thr Val Ser Ser Gly Gly Gly Gly Ser Gly Gly Gly
            115                 120                 125

Gly Ser Gly Gly Gly Gly Ser Asp Ile Glu Leu Thr Gln Ser Pro Ile
130                 135                 140

Gly Gln Val Gly Asn Lys Thr Gly Pro Lys Leu Glu Ile Lys Arg Ala
145                 150                 155                 160

Ala Ala Gly Ala Pro Val Pro Tyr Pro Asp Pro Leu Glu Pro Arg Ala
```

-continued

```
                     165                 170                 175
Ala

<210> SEQ ID NO 22
<211> LENGTH: 7
<212> TYPE: PRT
<213> ORGANISM: Artificial
<220> FEATURE:
<223> OTHER INFORMATION: Synthetic Linker

<400> SEQUENCE: 22

Gly Gly Gly Gly Ser Ser Ser
1               5
```